(12) United States Patent
Bezwada

(10) Patent No.: US 8,093,420 B2
(45) Date of Patent: Jan. 10, 2012

(54) FUNCTIONALIZED AMINO ACIDS AND ABSORBABLE POLYMERS THEREFROM

(75) Inventor: Rao S. Bezwada, Hillsborough, NJ (US)

(73) Assignee: Bezwada Biomedical, LLC, Hillsborough, NJ (US)

( * ) Notice: Subject to any disclaimer, the term of this patent is extended or adjusted under 35 U.S.C. 154(b) by 740 days.

(21) Appl. No.: 12/089,106

(22) PCT Filed: Oct. 10, 2006

(86) PCT No.: PCT/US2006/039501
§ 371 (c)(1),
(2), (4) Date: Sep. 23, 2008

(87) PCT Pub. No.: WO2007/047244
PCT Pub. Date: Apr. 26, 2007

(65) Prior Publication Data
US 2009/0098180 A1 Apr. 16, 2009

Related U.S. Application Data

(60) Provisional application No. 60/726,341, filed on Oct. 12, 2005.

(51) Int. Cl.
*C07C 229/00* (2006.01)
(52) U.S. Cl. .............. 560/40; 560/37; 560/42; 562/445; 562/442; 562/448
(58) Field of Classification Search ........................ None
See application file for complete search history.

(56) References Cited

U.S. PATENT DOCUMENTS

| | | | |
|---|---|---|---|
| 3,044,942 | A | 7/1962 | Baptist |
| 3,297,033 | A | 1/1967 | Schmitt |
| 3,371,069 | A | 2/1968 | Miyamae |
| 3,531,561 | A | 9/1970 | Trehu |
| 3,636,956 | A | 1/1972 | Schneider |
| 3,763,218 | A | 10/1973 | Kaiser et al. |
| 3,773,737 | A | 11/1973 | Goodman |
| 4,052,988 | A | 10/1977 | Doddi |
| 5,099,060 | A | 3/1992 | Kohn |
| 5,658,995 | A | 8/1997 | Kohn |
| 2005/0165203 | A1 | 7/2005 | Kohn |

FOREIGN PATENT DOCUMENTS
WO 2007/030538 A2 3/2007

OTHER PUBLICATIONS

Database Caplus Chemical Abstracts Service, Columbus, Ohio, US; Database Accession No. 1977:536203, Abstract of Livshits et al.: Zhurnal Obshchei Khimii (1977), 47(3), 699-709.*
Database Caplus Chemical Abstracts Service, Columbus, Ohio, US; Database Accession No. 1972:60075, Abstract of Kaiser et al.: DE 2122485.*
EP 06816592.7 European Extended Search Report.
PCT/US2006/039501 International Preliminary Report on Patentability.
Remington's Pharmaceutical Sciences, 18th ed., Mack Publishing Company, Eason, PA, 1990, p. 1445.
Gutowska et al, J. Biomater. Res., 29, 811-21 (1995).
Hoffman, J. Controlled Release, 6, 297-305 (1987).
Mikos et al, Biomaterials, 14, 323-329 (1993).
Schugens et al, J. Biomed. Mater. Res., 30, 449-462 (1996).
Bulletin of the Material Research Society, Special Issue on Tissue Engineering (Guest Editor: Joachim Kohn), 21(11), 22-26 (1996).
Helder et al, J. Biomed. Mater. Res., (24), 1005-1020 (1990).
Barrera et al, Macromolecules, (28), 425-432 (1995).

* cited by examiner

*Primary Examiner* — Karl J Puttlitz
(74) *Attorney, Agent, or Firm* — Vance Intellectual Property, PC

(57) ABSTRACT

The present invention relates to compounds of formula I and II, which are functionalized amino acids, and polymers formed from the same.

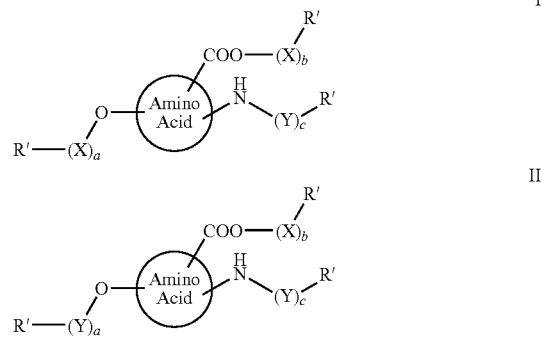

Polymers formed from the functionalized amino acids are expected to have controllable degradation profiles, enabling them to release an active component over a desired time range. The polymers are also expected to be useful in a variety of medical applications.

12 Claims, No Drawings

FUNCTIONALIZED AMINO ACIDS AND ABSORBABLE POLYMERS THEREFROM

FIELD OF THE INVENTION

The present invention relates to functionalized amino acids, especially phenol containing amino acids, and absorbable polymers derived there from, which can be useful for drug delivery, tissue engineering, stent coatings, stents, and implantable medical devices.

BACKGROUND OF THE INVENTION

Amino acids are the "building blocks" of the body. Besides building cells and repairing tissue, they form antibodies to combat invading bacteria & viruses; they are part of the enzyme & hormonal system; they build nucleoproteins (RNA & DNA); they carry oxygen throughout the body and participate in muscle activity. When a protein is broken down by digestion the result is 22 known amino acids. Eight are essential (cannot be manufactured by the body) the rest are non-essential (can be manufactured by the body with proper nutrition). Tyrosine is one of the non-essential amino acid. Tyrosine transmits nerve impulses to the brain; helps overcome depression; improves memory; increases mental alertness; and promotes the healthy functioning of the thyroid, adrenal, and pituitary glands.

U.S. Pat. No. 5,099,060 describes diphenolic monomers based on 3-(4-hydroxyphenyl) propionic acid and L-tyrosine alkyl esters (desaminotyrosyl-tyrosine alkyl esters). Subsequent related patents involve variations of this basic monomer structure. These monomers, although useful in many applications, have several limitations. The monomers are insoluble in water, and therefore the polymers made from them are not readily resorbable. In other words, the previously described polymers prepared from the previously described water-insoluble monomers will not have any weight loss while the degradation of the polymer backbone results in the loss of mechanical strength and reduction in the polymer molecular weight. The monomers also provide two phenolic hydroxyl groups, limiting the resulting polymers to be fully aromatic backbone structures, which may lead to good mechanical strength but slow degradation rate.

Poly(hydroxy acids), such as poly(glycolic acid) (PGA), poly(lactic acid) (PLA) and their copolymers are certainly the most widely investigated synthetic, degradable polymers due to their established record of safety and FDA approval. Poly (amino acids) derived from naturally occurring .alpha.-L-amino acids form another major group of degradable polymers. Despite their apparent potential as biomaterials, poly(amino acids) have actually found few practical applications. A major problem is that most of the poly(amino acids) are highly intractable (e.g., non-processable), which limits their utility.

Although several copolymers of hydroxy acids and amino acids have been prepared and evaluated from a biological perspective, their investigation as biomaterials has been rather limited. Helder et al., J. Biomed. Mater. Res., (24), 1005-1020 (1990) discloses the synthesis of glycine and DL-lactic acid copolymers and the resulting in vitro and in vivo degradation. The elegant synthesis of a copolymer derived from lactic acid and lysine was reported by Barrera et al., Macromolecules, (28), 425-432 (1995). The lysine residue was utilized to chemically attach a cell-adhesion promoting peptide to the copolymer. Other polymers of amino acids and hydroxy acids are disclosed by U.S. Pat. No. 3,773,737.

The three types of copolymers mentioned above are random copolymers prepared from cyclic monomers by ring-opening polymerization. The composition of the copolymers is highly dependent on the relative reactivity of the two types of cyclic monomers and on the exact polymerization conditions used. It is hard to control the composition and hard to predict the polymer properties. Also, there may be large batch-to-batch variations in the polymer microstructure and sequence. Furthermore, most previous reports described polymers of low molecular weight ($M_w$<10,000).

There are only a few degradable polymers for medical uses that have been successfully commercialized. Poly(glycolic acid) (PGA), poly(lactic acid) (PLA), and their copolymers are representative examples. In view of the limitations of these polymers, there still remains a need for biodegradable, especially bioresorbable, polymers suitable for use as tissue-compatible materials. For example, many investigators in the emerging field of tissue engineering have proposed to engineer new tissues by transplanting isolated cell populations on biomaterial scaffolds to create functional new tissues in vivo. Bioresorbable materials, whose degradation and resorption rates can be tailored to correspond to the rate of tissue growth, are needed.

SUMMARY OF THE INVENTION

The present invention provides novel functionalized amino acids, which are hydrolysable and can be useful for medical applications (e.g., drug delivery and solvent for dissolving drugs).

The present invention also provides novel, absorbable polymers and co-polymers (e.g., polyesters, polyamides, polyester amides, polyurethanes, and polyanhydrides) derived from functionalized amino acids. These polymers are expected to have controllable degradation profiles.

The present invention also provides novel medical devices comprising functionalized amino acids or polymers derived from functionalized amino acids.

Other features of the present invention will be pointed out in the following description and claims.

DETAILED DESCRIPTION OF THE INVENTION

Poly(hydroxy acids), such as PGA and PLA, are the most successful synthetic biomaterials. However, there are concerns about the acidity of their degradation products, their limited range of physicomechanical properties, and their simple chemical structure that does not provide chemical attachment points for biological ligands, drugs, or crosslinkers.

The present invention introduces novel functionalized amino acids and absorbable polymers derived from them. The amino acids are functionalized with safe and biocompatible molecules (e.g., glycolic acid, lactic acid, caprolactone, and dioxanone). The novel functionalized amino acids of the present invention are expected to have controllable hydrolysis profiles, improved bioavailability, improved efficacy, and enhanced functionality. Some of the functionalized amino acids can be monomers from which polymers can be made that are useful for medical applications. For example, phenol containing amino acids (e.g., L-tyrosine) can be functionalized to form functionalized monomers that can then be polymerized to form absorbable polymers (e.g., polyesters, polyamides, polyester amides, polyurethanes, and polyanhydrides). It can be advantageous for the monomers that are to be polymerized to have at least two active sites (e.g., 2 or 3) for polymerization. These active sites include hydroxyl, amino, and carboxylic acid groups (e.g., two hydroxyl groups, a hydroxyl group and a carboxylic acid, a hydroxyl group and an amine group, a carboxylic acid group and an amino group, and two carboxylic acid groups). The functionalized amino acids with at least two active sites can also be copolymerized with selected difunctional molecules (e.g., dicarboxylic acids, dialcohols, diisocyanates, amino-alcohols, hydroxy-carboxylic acids, and diamines) based on the starting functionalized amino acid to form absorbable polymers. The polymers (and copolymers) of the present invention can also be further reacted/polymerized to form additional useful polymers of the present invention.

The definitions and examples provided in this application are not intended to be limiting, unless specifically stated.

As described herein, the functionalized amino acids and polymers of the present invention are useful in medical applications/medical devices. Medical application/medical devices, as used herein, encompass medical and biomedical applications and include all types of applications involved in the practice of medicine that would benefit from a material that decomposes harmlessly within a known period of time. Examples include medical and surgical devices, which include drug delivery systems (e.g., a site-specific or systemic drug delivery systems or matrices), tissue engineering (e.g., tissue scaffold), stent coatings, stents, porous devices, implantable medical devices, molded articles (e.g., vascular grafts, stents, bone plates, sutures, implantable sensors, and barriers for surgical adhesion prevention), wound closure devices (e.g., surgical clips, staples, and sutures), coatings (e.g., for endoscopic instruments, sutures, stents, and needles), fibers or filaments (which may be attached to surgical needles or fabricated into materials including sutures or ligatures, multifilament yarn, sponges, gauze, tubes, and sheets for typing up and supporting damaged surface abrasions), rods, films (e.g., adhesion prevention barriers), knitted products, foodstuffs, nutritional supplements, nutriceuticals, cosmetics, pharmaceuticals, biodegradable chewing gums, flavors, enhanced drugs, drug intermediates, cancer preventing agents, antioxidants, controlled release preparations, and solvents for drugs. Examples of knitted products, woven or non-woven, and molded products include: burn dressings; hernia patches; medicated dressings; fascial substitutes; gauze, fabric, sheet, felt, or sponge for liver hemostasis; gauze bandages; arterial graft or substitutes; bandages for skin surfaces; suture knot clip; orthopedic pins, clamps, screws, and plates; clips (e.g., for vena cava); staples; hooks, buttons, and snaps; bone substitutes (e.g., mandible prosthesis); intrauterine devices (e.g., spermicidal devices); draining or testing tubes or capillaries; surgical instruments; vascular implants or supports; vertebral discs; extracorporeal tubing for kidney and heart-lung machines; and, artificial skin.

As used herein, "polymer" includes both polymers and copolymers depending on the number of different monomers used.

The present invention provides novel functionalized amino acids of formulas I and II or stereoisomers or pharmaceutically acceptable salts thereof:

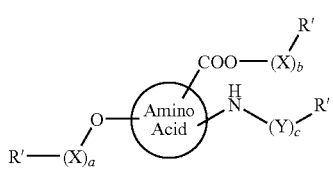

I

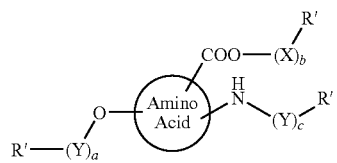

II wherein:

X is selected from:
— $CH_2COO$— (glycolic acid moiety);
— $CH(CH_3)COO$— (lactic acid moiety);
— $CH_2CH_2OCH_2COO$— (dioxanone moiety);
— $CH_2CH_2CH_2CH_2CH_2COO$— (caprolactone moiety);
— $(CH_2)_yCOO$— where y is selected from 2, 3, 4, 6, 7, 8, 9, 10, 11, 12, 13, 14, 15, 16, 17, 18, 19, 20, 21, 22, 23, and 24; and,
— $(CH_2CH_2O)_zCH_2COO$— where z is selected from 2, 3, 4, 5, 6, 7, 8, 9, 10, 11, 12, 13, 14, 15, 16, 17, 18, 19, 20, 21, 22, 23, and 24;

Y is selected from:
— $COCH_2O$— (glycolic ester moiety);
— $COCH(CH_3)O$— (lactic ester moiety);
— $COCH_2OCH_2CH_2O$— (dioxanone ester moiety);
— $COCH_2CH_2CH_2CH_2CH_2O$— (caprolactone ester moiety);
— $CO(CH_2)_mO$— where m is selected from 2, 3, 4, 6, 7, 8, 9, 10, 11, 12, 13, 14, 15, 16, 17, 18, 19, 20, 21, 22, 23, and 24; and,
— $COCH_2$—$O$—$(CH_2CH_2O)_n$— where n is selected from 2, 3, 4, 5, 6, 7, 8, 9, 10, 11, 12, 13, 14, 15, 16, 17, 18, 19, 20, 21, 22, 23, and 24;

R' is selected from H, benzyl, and $C_{1-6}$ alkyl;

a, b, and c, are independently selected from 0, 1, 2, 3, 4, provided that a+b+c total from 1, 2, 3, 4, 5, to 6;

Amino acid is a phenol-containing amino acid;

alternatively, when 1 or 2 of a, b, and c are 0, then "O—$(X)_b$" is NR'; and, alternatively, when 1 or 2 of a, b, c are 0, then "$(Y)_c$" is C(O), further provided that when "$(Y)_c$" is C(O), then R' is other than H;

provided that:
a. in formula I, when $(X)_bR'$=H and $(Y)_cR'$=H, then $(X)_aR'$ is other than $CH_2C(O)OH$;
b. in formula I, when $(X)_aR'$=H and $(X)_bR'$=H, then $(Y)_cR'$ is other than $C(O)CH_2OH$; and,
c. in formula II, when $(Y)_aR'$=H and $(X)_bR'$=H, then $(Y)_cR'$ is other than $C(O)CH_2OH$.

The group represented by X is attached via its carbon terminus to the oxygen group of the amino acid. The group represented by Y is attached via its carbonyl terminus to the oxygen or nitrogen group of the amino acid.

The rate of hydrolysis of the functionalized amino acids will depend upon a number of factors, including the functionalization species used and the number of functionalization species present on the functionalized amino acid (e.g., 1-6). Glycolic acid modified amino acids should hydrolyze faster than dioxanone modifies ones, where as lactic acid and caprolactone modified amino acids should take much longer to hydrolyze than glycolic acid and dioxanone modified amino acids. Furthermore, it is expected that the rate of hydrolysis will increase with the increase in the value of a+b+c. Thus, the desired time range may be obtained by altering the number and type of functionalization species used to functionalize the amino acid.

The present invention provides novel functionalized amino acids of formulas I and II, wherein the amino acid is selected from tyrosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, 1,2,3,4-tetrahydroxyisoquinoline-7-hydroxy-3-carboxylic acid, thyronine, 3,4-dihydroxyphenylalanine, 4-hydroxyphenylglycine, 3-aminosalicylic acid; 4-aminosalicylic acid; and 5-aminosalicylic acid.

The amino acids used in the present invention include all of the possible stereoisomers (e.g., D, L, D/L), unless a specific isomer is identified.

The present invention also provides novel functionalized amino acids of formulas I and II wherein y is selected from 2, 3, and 4; z is selected from 2, 3, and 4; m is selected from 2, 3, and 4; and n is selected from 2, 3, and 4.

The present invention also provides novel functionalized amino acids of formulas I and II, wherein:
X is selected from:
—$CH_2COO$—;
—$CH(CH_3)COO$—;
—$CH_2CH_2OCH_2COO$—; and,
—$CH_2CH_2CH_2CH_2CH_2COO$—;
Y is selected from:
—$COCH_2O$—;
—$COCH(CH_3)O$—;
—$COCH_2OCH_2CH_2O$—;
—$COCH_2CH_2CH_2CH_2CH_2O$—; and,
a, b, and c, are independently selected from 0-2, provided that a+b+c total from 1-4.

The present invention also provides novel functionalized amino acids of formulas I and II, wherein:
R' is selected from H, benzyl, and $C_{1-4}$ alkyl; and,
a, b, and c, are independently selected from 0-2, provided that a+b+c total from 1-3.

The present invention also provides novel functionalized amino acids of formulas I and II, wherein:
R' is selected from H, benzyl, and $CH_3$; and,
a, b, and c, are independently selected from 0-1, provided that a+b+c total from 1-3.

The present invention also provides novel functionalized amino acids of formulas I and II, wherein:
X is —$CH_2COO$—;
Y is —$COCH_2O$—;
R' is selected from H, benzyl, and $C_{1-4}$ alkyl; and,
a, b, and c, are independently selected from 0-2, provided that a+b+c total from 1-4.

The present invention also provides novel functionalized amino acids of formulas I and II, wherein:
the compound is of formula I;
R' is selected from H, benzyl, and $CH_3$; and,
a, b, and c, are independently selected from 0-1, provided that a+b+c total from 1-3.

The present invention also provides novel functionalized amino acids of formulas Ia and IIa, wherein:

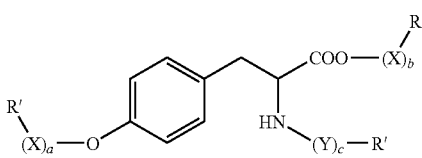

Ia

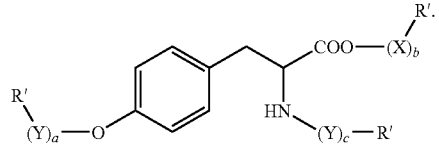

IIa wherein:
X is selected from:
—$CH_2COO$— (glycolic acid moiety);
—$CH(CH_3)COO$— (lactic acid moiety);
—$CH_2CH_2OCH_2COO$— (dioxanone moiety);
—$CH_2CH_2CH_2CH_2CH_2COO$— (caprolactone moiety);
—$(CH_2)_yCOO$— where y is selected from 2, 3, 4, 6, 7, 8, 9, 10, 11, 12, 13, 14, 15, 16, 17, 18, 19, 20, 21, 22, 23, and 24; and,
—$(CH_2CH_2O)_zCH_2COO$— where z is selected from 2, 3, 4, 5, 6, 7, 8, 9, 10, 11, 12, 13, 14, 15, 16, 17, 18, 19, 20, 21, 22, 23, and 24;
Y is selected from:
—$COCH_2O$— (glycolic ester moiety);
—$COCH(CH_3)O$— (lactic ester moiety);
—$COCH_2OCH_2CH_2O$— (dioxanone ester moiety);
—$COCH_2CH_2CH_2CH_2CH_2O$— (caprolactone ester moiety);
—$CO(CH_2)_mO$— where m is selected from 2, 3, 4, 6, 7, 8, 9, 10, 11, 12, 13, 14, 15, 16, 17, 18, 19, 20, 21, 22, 23, and 24; and,
—$COCH_2$—O—$(CH_2CH_2O)_n$— where n is selected from 2, 3, 4, 5, 6, 7, 8, 9, 10, 11, 12, 13, 14, 15, 16, 17, 18, 19, 20, 21, 22, 23, and 24;
R' is selected from H, benzyl, and $C_{1-6}$ alkyl; and,
a, b, and c, are independently selected from 0, 1, 2, 3, 4, provided that a+b+c total from 1, 2, 3, 4, 5, to 6;
alternatively, when 1 or 2 of a, b, and c are 0, then "O—$(X)_b$" is NR'; and,
alternatively, when 1 or 2 of a, b, c are 0, then "$(Y)_c$" is C(O), further provided that when "$(Y)_c$" is C(O), then R' is other than H;
provided that:
a. in formula I, when $(X)_bR'$=H and $(Y)_cR'$=H, then $(X)_3R'$ is other than $CH_2C(O)OH$;
b. in formula I, when $(X)_3R'$=H and $(X)_bR'$=H, then $(Y)_cR'$ is other than $C(O)CH_2OH$; and,
c. in formula II, when $(Y)_3R'$=H and $(X)_bR'$=H, then $(Y)_cR'$ is other than $C(O)CH_2OH$.

The present invention also provides novel functionalized amino acids of formulas Ia and IIa, wherein:
X is selected from:
—$CH_2COO$—;
—$CH(CH_3)COO$—;
—$CH_2CH_2OCH_2COO$—; and,
—$CH_2CH_2CH_2CH_2CH_2COO$—;
Y is selected from:
—$COCH_2O$—;
—$COCH(CH_3)O$—;
—$COCH_2OCH_2CH_2O$—;
—$COCH_2CH_2CH_2CH_2CH_2O$—; and,
a, b, and c, are independently selected from 0-2, provided that a+b+c total from 2-4.

The present invention also provides novel functionalized amino acids of formulas Ia and IIa, wherein:
R' is selected from H, benzyl, and $CH_3$; and,
a, b, and c, are independently selected from 0-1, provided that a+b+c total from 2-3.

The present invention also provides novel functionalized amino acids of formulas Ia and IIa, wherein:
X is —CH$_2$COO—;
Y is —COCH$_2$O—;
R' is selected from H, benzyl, and C$_{1-4}$ alkyl; and,
a, b, and c, are independently selected from 0-2, provided that a+b+c total from 2-4.

The present invention also provides novel functionalized amino acids of formulas Ia and IIa, wherein:
the compound is of formula Ia;
R' is selected from H, benzyl, and CH$_3$; and,
a, b, and c, are independently selected from 0-1, provided that a+b+c total from 2-3.

Some examples of functionalized L-tyrosine molecules include the following or stereoisomers or pharmaceutically acceptable salts thereof.

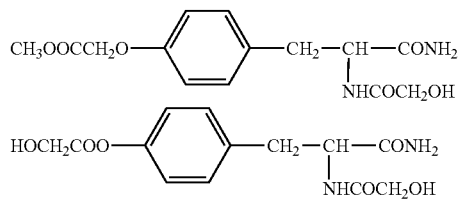

The functionalized amino acids of the present invention can be polymerized via conventional polymerization process using diol, triols, dicarboxylic acids, tricarboxylic acids, diamines, or triamines based on the starting difunctionalized or trifunctionalized amino acids, including those processes that synthesize polymers traditionally considered hydrolytically stable and non-biodegradable.

The monomers of the present invention may be polymerized to form absorbable polymers that display excellent physical, chemical, and biological properties, which make them useful in medical applications. In addition to being non-toxic in polymer form, the polymers of the present invention are expected to form non-toxic degradation products by hydrolytic chain cleavage under physiological conditions. The novel polymers of the present invention are expected to have increased rate of degradation and bioresorption as well as controllable degradation profile in comparison to the currently available polymers.

For example, a phenol containing amino acid, such as L-tyrosine, can be functionalized to form a reactive compound, which can be polymerized to form an absorbable polymer with a specific absorption profile. Similarly, each phenol containing amino acid described above can be functionalized to form reactive monomers. The polymers derived from these monomers will have unique physical and biological properties with absorption profiles that are controllable.

The absorbable polymers (e.g., polyesters, polyamides, polyester amides, polyurethanes, and polyanhydrides) of the present invention should degrade faster and bioresorb faster than prior art polycarbonates and polyarylates polymerized from desaminotyrosyltyrosine alkyl esters (see U.S. Pat. Nos. 5,099,060, and 5,658,995). The polymers of the present invention are therefore expected to be useful as biomaterials in those situations that require a faster degradation and resorption rate than the previously achieved by known polymers of amino acids. Specific examples of applications for which the polymers of the present invention should be particularly useful include scaffolds for tissue engineering on which isolated cell populations may be transplanted in order to engineer new tissues and implantable drug delivery devices where a pharmaceutically active moiety is admixed or in some way located within the polymeric matrix for slow release.

The present invention encompasses a variety of different polymers, some of which are copolymers. The polymers of the present invention include (a) polymers formed from one functionalized amino acid; (b) copolymers formed from more than one (e.g., 2, 3, or 4) type of functionalized amino acid (e.g., a blend of functionalized amino acids that is polymerized); (c) copolymers formed from at least one type of functionalized amino acid having at least two active sites (e.g, 2 or 3) and a difunctional molecule (e.g., dicarboxylic acids, dialcohols, diisocyanates, amino-alcohols, hydroxycarboxylic acids, and diamines); and (d) copolymers formed from at least one of the polymers of (a)-(c) and at least one lactone monomer (e.g., glycolide, lactide, ε-caprolactone, trimethylene carbonate, and p-dioxanone). The absorption profile of the polymers of the present invention will depend upon a number of factors, including the functionalization species used and the number of functionalization species present on the functionalized amino acid (e.g., 1-6). Glycolic acid based polymers should hydrolyze faster than dioxanone based, where as lactic acid and caprolactone based polymers should take much longer to hydrolyze than glycolic acid and dioxanone based polymers. The desired time range may be obtained by altering the number and type of functionalization species as well as the number of different functionalized amino acids (e.g., a blend of two or more functionalized amino acids). The desired time range will also be impacted by moieties used for co-polymerization (e.g., difunctional compounds or lactone monomers).

As noted above, the functionalized amino acids of the present invention can be polymerized to form absorbable functionalized amino acid polymers of the present invention. If a linear polymer is desired, then only one active site is preferably present on the functionalized amino acid. Thus, if a linear polymer is desired from a functionalized amino acid wherein (X)$_b$—R'=H (i.e., b=0 and R'=H) and (Y)$_c$—R' is H (i.e., c=0 and R'=H), then it is advantageous to amidate either or both of the unmodified COOH and NH$_2$ groups. For example, O—(X)$_b$—R' can be converted to NR'R' and/or (Y)$_c$—R' can be converted to C(O)R' (provided that when (Y)$_c$ is C(O), then R' is other than H).

The functionalized amino acid polymers can be used in various medical applications described herein or can be further polymerized with lactone monomers, such as glycolide, lactide, ε-caprolactone, trimethylene carbonate, and p-dioxanone, and the resulting absorbable functionalized amino acid/lactone copolymers can be used in the various medical applications described herein.

As noted above, more than one of the functionalized amino acids of the present invention can be blended and polymerized to form a functionalized amino acid copolymer. The functionalized amino acid copolymers can be used in various medical applications described herein or can be further polymerized with lactone monomers, such as glycolide, lactide, ε-caprolactone, trimethylene carbonate, and p-dioxanone, and the resulting absorbable polymers can also have the medical applications described herein.

As noted above, the functionalized amino acids of the present invention with at least two reactive sites can be polymerized with difunctional molecules (e.g., dicarboxylic acids, dialcohols, diisocyanates, amino-alcohols, hydroxycarboxylic acids, and diamines) to form absorbable polymers, including but not limited to polyesters, polyester amides, polyurethanes, polyamides, and polyanhydrides by simple polycondensation reactions. The functionalized amino acid/ difunctional molecule polymers can be used in various medical applications or can be further polymerized with lactone monomers, such as glycolide, lactide, ε-caprolactone, trimethylene carbonate, and p-dioxanone, and the resulting absorbable polymers potential have the medical applications described above.

In another example of the present invention, functionalized dihydroxy amino acids of the present invention can be used in the preparation of polyesters by reacting with dicarboxylic acid compounds. Dicarboxylic acids useful in the present invention have the following structure:

HOOC—R—COOH wherein R is selected from saturated and unsaturated, substituted and unsubstituted alkyl, aryl and alkylaryl groups having from 1, 2, 3, 4, 5, 6, 7, 8, 9, 10, 11, 12, 13, 14, 15, 16, 17, and 18 carbon atoms In another example of the present invention, functionalized dicarboxylic acid amino acids of the present invention can be used in the preparation of polyesters by reacting with the dialcohol (i.e., diol) compounds. Dialcohols useful in the present invention have the following structure:

HO—R—OH wherein R is selected from saturated and unsaturated, substituted and unsubstituted alkyl, aryl and alkylaryl groups having from 2, 3, 4, 5, 6, 7, 8, 9, 10, 11, 12, 13, 14, 15, 16, 17, and 18 carbon atoms. Alternatively, polyalkylene oxides have weight average molecular weights from about 500-5,000 can be used as a diol (i.e., a polydiol). Suitable diols or polydiols for use in the present invention are diol or diol repeating units with up to 8 carbon atoms. Examples of suitable diols include 1,2-ethanediol (ethylene glycol); 1,2-propanediol (propylene glycol); 1,3-propanediol; 1,4-butanediol; 1,5-pentanediol; 1,3-cyclopentanediol; 1,6-hexanediol; 1,4-cyclohexanediol; 1,8-octanediol; and, combinations thereof. Examples of polydiols include polyethylene glycol and polypropylene glycol with weight average molecular weights of 500-5000.

In another example of the present invention, functionalized dihydroxy amino acids of the present invention can be used in the preparation of polyurethanes by reacting with diisocyante compounds. Examples of diisocyanates include hexamethylene diisocyante, lysine diisocyanate, methylene diphenyl diisocyanate (e.g., MDI), hydrogenated MDI (e.g., methylene dicyclohexyl diisocyanate), and isophorone diisocyanate.

In another example of the present invention, functionalized hydroxy-amino amino acids of the present invention can be used in the preparation of polyesteramides by reacting with dicarboxylic acid compounds described above.

In another example of the present invention, functionalized dicarboxylic acid amino acids of the present invention can be used in the preparation of polyesteramides by reacting with the amino-alcohol compounds. Amino-alcohols useful in the present invention have the following structure:

HO—R—NH₂ wherein R is selected from saturated and unsaturated, substituted and unsubstituted alkyl, aryl and alkylaryl groups having from 2, 3, 4, 5, 6, 7, 8, 9, 10, 11, 12, 13, 14, 15, 16, 17, and 18 carbon atoms.

In another example of the present invention, functionalized hydroxy-carboxylic acid amino acids of the present invention can be used in the preparation of polyesters by reacting with hydroxycarboxylic acid compounds. Hydroxycarboxylic acids useful in the present invention have the following structure:

HO—R—COOH wherein R is selected from saturated and unsaturated, substituted and unsubstituted alkyl, aryl and alkylaryl groups having from 1, 2, 3, 4, 5, 6, 7, 8, 9, 10, 11, 12, 13, 14, 15, 16, 17, and 18 carbon atoms, In another example of the present invention, functionalized amino-carboxylic acid amino acids of the present invention can be used in the preparation of polyesteramides by reacting with the hydroxycarboxylic acid compounds described above.

In another example of the present invention, functionalized dicarboxylic acid amino acids of the present invention can be used in the preparation of polyamides by reacting with the diamine compounds. Diamines useful in the present invention have the following structure:

H₂N—R—NH₂ wherein R is selected from saturated and unsaturated, substituted and unsubstituted alkyl, aryl and alkylaryl groups having from 2, 3, 4, 5, 6, 7, 8, 9, 10, 11, 12, 13, 14, 15, 16, 17, and 18 carbon atoms. Alternatively, polyalkylene oxides that are diamines with weight average molecular weights from about 500-5,000 can be used.

In another example of the present invention, functionalized dicarboxylic acid amino acids of the present invention can be used in the preparation of polyanhydrides by reacting with the dicarboxylic acid compounds described above.

The functionalized amino acids of the present invention having more than two reactive groups (e.g., 3) are expected to be useful in the preparation of cross linked hydrogels and are prepared Examples of polymers of the present invention have weight-average molecular weights above about 20,000 daltons or above about 100,000 daltons, calculated from gel permeation chromatography (GPC) relative to polystyrene standards in tetrahydrofuran (THF) without further correction.

The polymers of the present invention should be able to be processed by known methods commonly employed in the field of synthetic polymers to provide a variety of useful articles with valuable physical and chemical properties. The useful articles can be shaped by conventional polymer-forming techniques such as extrusion, compression molding, injection molding, solvent casting, and wet spinning. Shaped articles prepared from the polymers are expected to be useful as degradable devices for medical implant applications.

The present invention also relates to a composition, comprising: two or more functional amino acids of the present invention.

The present invention also relates to a composition, comprising: at least one functionalized amino acid, wherein the composition is suitable for use as at least one of the following: (a) a solvent for drugs; (b) a nutritional compound; (c) a cosmetic: and, (d) a pharmaceutical. Each of the compositions may further comprise an additional component suitable for such composition. For example, when the composition is suitable for use as a cosmetic it may further comprise: one or more cosmetic ingredients. Also, when the composition is suitable for use as a pharmaceutical it may further comprise: one or more pharmaceutically acceptable excipients.

The implantable medical devices of the present invention, comprise: at least one absorbable polymer of the present invention. For example, a polymer of the present invention can be combined with a quantity of a biologically or pharmaceutically active compound sufficient to be therapeutically effective as a site-specific or systemic drug delivery system (see Gutowska et al., J. Biomater. Res., 29, 811-21 (1995) and Hoffman, J. Controlled Release, 6, 297-305 (1987)). Another example of the present invention is a method for site-specific or systemic drug delivery by implanting in the body of a patient in need thereof an implantable drug delivery device comprising a therapeutically effective amount of a biologically or a physiologically active compound in combination with at least one absorbable polymer of the present invention.

In another example, at least one polymer of the present invention is formed into a porous device (see Mikos et al., Biomaterials, 14, 323-329 (1993) or Schugens et al., J. Biomed. Mater. Res., 30, 449-462 (1996)) to allow for the attachment and growth of cells (see Bulletin of the Material Research Society, Special Issue on Tissue Engineering (Guest Editor: Joachim Kohn), 21(11), 22-26 (1996)). Thus, the present invention provides a tissue scaffold comprising a porous structure for the attachment and proliferation of cells either in vitro or in vivo formed from at least one absorbable polymer of the present invention The present invention also relates to an article (e.g., an implantable medical device), comprising: a metal or polymeric substrate having thereon a coating, wherein the coating, comprises: at least one polymer of the present invention.

The present invention also relates to a molded article prepared from at least one polymer of the present invention.

The present invention also relates to a controlled drug delivery system, comprising: at least one polymer of the present invention physically admixed with a biologically or pharmacologically active agent. For example, the controlled drug delivery system can comprise: a biologically or pharmacologically active agent coated with at least one polymer of the present invention.

The present invention also relates to a controlled drug delivery system, comprising: a biologically or pharmacologically active agent physically embedded or dispersed into a polymeric matrix formed from at least one polymer of the present invention.

The present invention also relates to a tissue scaffold having a porous structure for the attachment and proliferation of cells, either in vitro or in vivo, formed from one least one polymer of the present invention.

The present invention also relates to a composition, comprising: at least one polymer of the present invention, which has been further polymerized with at least one lactone monomer selected from: glycolide, lactide, p-dioxanone, trimethylene carbonate, and caprolactone.

The present invention also relates to an implantable biomedical device, comprising: at least one polymer that has been further polymerized with at least one lactone monomer.

The present invention also relates to a biodegradable chewing gum composition, comprising: an effective amount of at least one polymer that has been further polymerized with at least on lactone monomer.

The present invention also relates to an article (e.g., an implantable medical device), comprising: a metal or polymeric substrate and having thereon a coating, wherein said coating comprises at least one polymer that has been further polymerized with at least one lactone monomer.

The present invention also relates to a molded article prepared from at least one polymer that has been further polymerized with at least one lactone monomer.

The present invention also relates to a monofilament or multifilament prepared from at least one polymer that has been further polymerized with at least one lactone monomer.

The present invention also relates to a controlled drug delivery system, comprising: at least one polymer that has been further polymerized with at least one lactone monomer, which has been physically admixed with a biologically or pharmacologically active agent.

The present invention also relates to a controlled drug delivery system, comprising: a biologically or pharmacologically active agent physically embedded or dispersed into a polymeric matrix formed from at least one polymer that has been further polymerized with at least one lactone monomer.

The present invention also relates to a tissue scaffold having a porous structure for the attachment and proliferation of cells, either in vitro or in vivo, formed from at least one polymer that has been further polymerized with at least one lactone monomer.

The present invention also relates to low molecular weight polymers or oligomers of the functionalized amino acids of the present invention that are further reacted to form reactive end groups (e.g., isocyanates, expoxides, and acrylates). Low-molecular weight polymers or oligomers as used herein means a polymer having a number average molecular weight of about 500-20,000 or 500-10,000. For example, some of the functionalized phenolic amino acids behave chemically like diols. They can be reacted with dicarboxylic acids to form polyesters, which are usually hydroxyterminated. These hydroxyterminated oligomers can be further reacted to form isocyanates, epoxides and acrylates. Similarly the functionalized phenolic amino acids can be reacted with isocyanates to make urethanes. Thus, the present invention also includes a composition, comprising: at least one polymer of the present invention, which has been further reacted to form reactive end groups.

The present invention also relates to polymers made from functionalized amino acids that have been sterilized by cobalt-60 radiation, electron beam radiation, and/or ethylene oxide.

"Bioabsorbable" or "absorbable" as used herein means that the material readily reacts or enzymatically degrades upon exposure to bodily tissue for a relatively short period of time, thereby experiencing a significant weight loss in that short period of time. Complete bioabsorption/absorption should take place within twelve months, although it may be complete within nine months or within six months. In this manner, the polymers of the present invention can be fabricated into medical and surgical devices, which are useful for a vast array of applications requiring complete absorption within a relatively short time period.

The biological properties of the bioabsorbable polymers of the present invention used to form a device or part thereof, as measured by its absorption rate and its breaking strength retention in vivo (BSR), can be varied to suit the needs of the particular application for which the fabricated medical device or component is intended. This can be conveniently accomplished by varying the ratio of components of the polymer chosen.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat the desired indication.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, s-pentyl, and n-hexyl.

Polymers of the present invention may be made in the form of random copolymers or block copolymers. A coupling agent may also be added to the polymers of the present invention. A coupling agent is a reagent that has a least two functional groups that are capable of covalently bonding to two different monomers. Examples of coupling agents include trifunctional or tetrafunctional polyols, oxycarboxylic acids, and polybasic carboxylic acids (or acid anhydrides thereof). Other coupling agents include the difunctional groups (e.g., diols, diacids, diamines, and hydroxy-acids) previously discussed. The addition of the coupling agents causes the branching of long chains, which can impart desirable properties in the molten state to the pre-polymer. Examples of polyfunctional coupling agents include trimethylol propane, glycerin, pentaerythritol, malic acid, citric acid, tartaric acid, trimesic acid, propane tricarboxylic acid, cyclopentane tetracarboxylic anhydride, and combinations thereof.

A "pre-polymer" is a low-molecular weight polymer, as previously defined, that have reactive endgroups (e.g., hydroxy groups) that can be further reactive with, for example, the lactone monomers.

The amount of coupling agent to be added before gelation occurs is a function of the type of coupling agent used and the polymerization conditions of the polymer or molecular weight of the pre-polymer to which it is added. Generally in the range of from about 0.1 to about 10 mole percent of a trifunctional or a tetrafunctional coupling agent may be added based on the moles of polymers present or anticipated from the synthesis.

The polymerization of a polyester of the present invention can be performed under melt polycondensation conditions in the presence of an organometallic catalyst at elevated temperatures. The organometallic catalyst can be a tin-based catalyst (e.g., stannous octoate or dibutyl tin oxide). The catalyst can be present in the mixture at a mole ratio of diol, dicarboxylic acid, and optionally lactone monomer to catalyst will be in the range of from about 15,000/1 to 80,000/1. The reaction can be performed at a temperature not less than about 120° C. under reduced pressure. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and the glass transition temperature and softening temperature of the polymer. Desired reaction conditions of temperature, time and pressure can be readily determined by assessing these and other factors. Generally, the reaction mixture will be maintained at about 220° C. The polymerization reaction can be allowed to proceed at this temperature until the desired molecular weight and percent conversion is achieved for the copolymer, which will typically take about 15 minutes to 24 hours. Increasing the reaction temperature generally decreases the reaction time needed to achieve a particular molecular weight.

Polymerization conditions for the preparation of other types of polymers of the present invention (e.g., polyamides and polyurethanes) are described in the literature. Those skilled in the art will recognize that the polymers described herein can be made from known procedures.

Copolymers of the absorbable polymers of the present invention can be prepared by preparing a pre-polymer under melt polycondensation conditions, then adding at least one lactone monomer or lactone pre-polymer. The mixture could then be subjected to the desired conditions of temperature and time to copolymerize the pre-polymer with the lactone monomers.

A lactone pre-polymer is a pre-polymer formed by ring opening polymerization with a known initiator (e.g., ethylene glycol, diethylene glycol, glycerol, or other diols or triols).

The molecular weight of the pre-polymer as well as its composition can be varied depending on the desired characteristic, which the pre-polymer is to impart to the copolymer. For example, the pre-polymers of the present invention, from which the copolymer is prepared, generally have a molecular weight that provides an inherent viscosity between about 0.2 to about 2.0 deciliters per gram (dl/g) as measured in a 0.1 g/dl solution of hexafluoroisopropanol at 25° C. Those skilled in the art will recognize that the pre-polymers described herein can also be made from mixtures of more than one diol or dicarboxylic acid.

One of the beneficial properties of the polyesters of the present invention is that the ester linkages are hydrolytically unstable, and therefore the polymer is bioabsorbable because it readily breaks down into small segments when exposed to moist bodily tissue. In this regard, while it is envisioned that co-reactants could be incorporated into the reaction mixture of the dicarboxylic acid and the diol for the formation of the polyester pre-polymer, it is preferable that the reaction mixture does not contain a concentration of any co-reactant which would render the subsequently prepared polymer nonabsorbable. The reaction mixture can be substantially free of any such co-reactants if the presence thereof results in a nonabsorbable polymer.

The polymers of the present invention can be melt processed by numerous methods to prepare a vast array of useful devices. These polymers can be injection or compression molded to make implantable medical and surgical devices, especially wound closure devices.

Alternatively, the polymers can be extruded to prepare fibers. The filaments thus produced may be fabricated into sutures or ligatures, attached to surgical needles, packaged, and sterilized by known techniques. The polymers of the present invention may be spun as multifilament yarn and woven or knitted to form sponges or gauze, (or non-woven sheets may be prepared) or used in conjunction with other molded compressive structures as prosthetic devices within the body of a human or animal where it is desirable that the structure have high tensile strength and desirable levels of compliance and/or ductility. Examples include tubes, including branched tubes, for artery, vein, or intestinal repair, nerve splicing, tendon splicing, sheets for typing up and supporting damaged surface abrasions, particularly major abrasions, or areas where the skin and underlying tissues are damaged or surgically removed.

Additionally, the polymers can be molded to form films which, when sterilized, are useful as adhesion prevention barriers. Another alternative processing technique for the polymers of the present invention includes solvent casting, particularly for those applications where a drug delivery matrix is desired.

The polymers of the present invention can be used to coat a surface of a surgical article to enhance the lubricity of the coated surface. The polymer may be applied as a coating using conventional techniques. For example, the polymer may be solubilized in a dilute solution of a volatile organic solvent (e.g. acetone, methanol, ethyl acetate, or toluene), and then the article can be immersed in the solution to coat its surface. Once the surface is coated, the surgical article can be removed from the solution where it can be dried at an elevated temperature until the solvent and any residual reactants are removed.

For coating applications, the polymer should exhibit an inherent viscosity, as measured in a 0.1 gram per deciliter (g/dl) of hexafluoroisopropanol (HFIP), between about 0.05-2.0 dl/g or about 0.10-0.80 dl/g. If the inherent viscosity were less than about 0.05 dl/g, then the polymer may not have the integrity necessary for the preparation of films or coatings for the surfaces of various surgical and medical articles. On the other hand, it is possible to use polymers with an inherent viscosity greater than about 2.0 dl/g, though it may be difficult to do so.

Although numerous surgical articles (including but not limited to endoscopic instruments) can be coated with the polymer of the present invention to improve the surface properties of the article, specific surgical articles include surgical sutures, stents, and needles. For example the surgical article can be a suture, which can be attached to a needle. The suture can be a synthetic absorbable suture. These sutures are derived, for example, from homopolymers and copolymers of lactone monomers such as glycolide, lactide, ε-caprolactone, 1,4-dioxanone, and trimethylene carbonate. The suture can be a braided multifilament suture composed of polyglycolide or poly(glycolide-co-lactide).

The amount of coating polymer to be applied on the surface of a braided suture can be readily determined empirically, and will depend on the particular copolymer and suture chosen. Ideally, the amount of coating copolymer applied to the surface of the suture may range from about 0.5-30 percent of the weight of the coated suture or from about 1.0-20 weight percent, or from 1-5 percent by weight. If the amount of coating on the suture were greater than about 30 weight percent, then it may increase the risk that the coating may flake off when the suture is passed through tissue Sutures coated with the polymers of the present invention are desirable because they have a more slippery feel, thus making it easier for the surgeon to slide a knot down the suture to the site of surgical trauma. In addition, the suture is more pliable, and therefore is easier for the surgeon to manipulate during use. These advantages are exhibited in comparison to sutures which do not have their surfaces coated with the polymer of the present invention.

When the article of the present invention is a metal stent, the amount of coating applied to the surface of the article is an amount which creates a layer with a thickness ranging, for example, between about 2-20 microns on the stent or about 4-8 microns. If the amount of coating on the stent were such that the thickness of the coating layer was greater than about 20 microns, or if the thickness was less than about 2 microns, then the desired performance of the stent as it is passed through tissue may not be achieved.

When the article of the present invention is a surgical needle, the amount of coating applied to the surface of the article is an amount which creates a layer with a thickness ranging, for example, between about 2-20 microns on the needle or about 4-8 microns. If the amount of coating on the needle were such that the thickness of the coating layer was greater than about 20 microns, or if the thickness was less than about 2 microns, then the desired performance of the needle as it is passed through tissue may not be achieved.

The polymers of the present invention can also be used as a pharmaceutical carrier in a drug delivery matrix. To form this matrix the polymer can be mixed with a therapeutic agent to form the matrix. There are a variety of different therapeutic agents, which can be used in conjunction with the polymers of the invention. In general, therapeutic agents which may be administered via the pharmaceutical compositions of the invention include, antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered in any suitable dosage form including orally, parenterally, subcutaneously as an implant, vaginally, or as a suppository. Matrix formulations containing the polymers of the present invention may be formulated by mixing one or more therapeutic agents with the polymer. The therapeutic agent, may be present as a liquid, a finely divided solid, or any other appropriate physical form. Typically, but optionally, the matrix will include one or more additives, e.g., nontoxic auxiliary substances such as diluents, carriers, excipients, or stabilizers. Other suitable additives may be formulated with the polymers of the present invention and pharmaceutically active agent. If water is to be used, then it can be useful to add it just before administration.

The amount of therapeutic agent will be dependent upon the particular drug employed and medical condition being treated. Typically, the amount of drug represents about 0.001%-70%, 0.001%-50%, or 0.001%-20% by weight of the matrix.

The quantity and type of polymer incorporated into a composition (e.g., parenterally delivered composition) will vary depending on the release profile desired and the amount of drug employed. The product may contain blends of polymers of the present invention to provide the desired release profile or consistency to a given formulation.

The polymers of the present invention, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (e.g., over 1-2,000 hours or 2-800 hours) of effective amounts (e.g., 0.0001 mg/kg/hour to 10 mg/kg/hour) of the drug. This dosage form can be administered as is necessary depending on the subject being treated, the severity of the affliction, and the judgment of the prescribing physician.

Individual formulations of drugs and polymers of the present invention may be tested in appropriate in vitro and in vivo models to achieve the desired drug release profiles. For example, a drug could be formulated with a polymer of the present invention and orally administered to an animal. The drug release profile could then be monitored by appropriate means such as, by taking blood samples at specific times and assaying the samples for drug concentration. Following this or similar procedures, those skilled in the art will be able to formulate a variety of formulations.

Functionalization

The functionalized amino acids of the present invention are typically prepared from a starting amino acid as shown below.

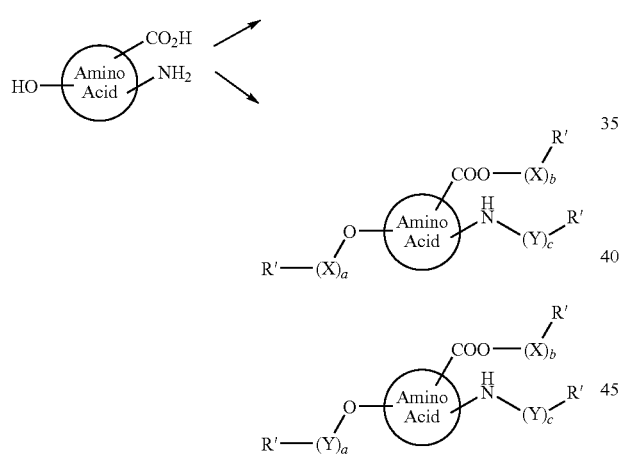

The desired X and Y groups can be added using methods known to those of skill in the art, some of which are described below.

Glycolic acid and lactic acid are also known as alpha hydroxy acids (AHA) present in fruits and other foods. These acids are present in many healthiest foods we eat and drink, and they are considered to be safe when used correctly. Glycolic acid occurs naturally as the chief acidic constituent of sugar cane juice and occurs in beet juice and unripe grapes. Its formula is $HOCH_2COOH$ and is biodegradable. When glycolic acid is heated it readily loses water by self-esterification to form polyglycolic acid. Glycolic acid can function as both an acid and an alcohol. The process of attaching a glycolic acid moiety to the phenolic amino acid is defined as glycolation and will be referred to as such in describing this invention:

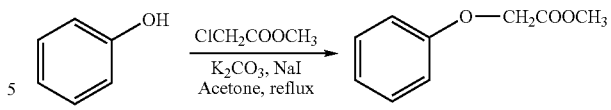

Lactic acid is a fermentation product of lactose. Lactic acid is produced commercially for use in foods and pharmaceuticals. Many surgical and orthopedic devices are made from polylactic acid. The process of attaching a lactic acid moiety to the phenolic amino acid is defined as lactolation and will be referred to as such in describing this invention:

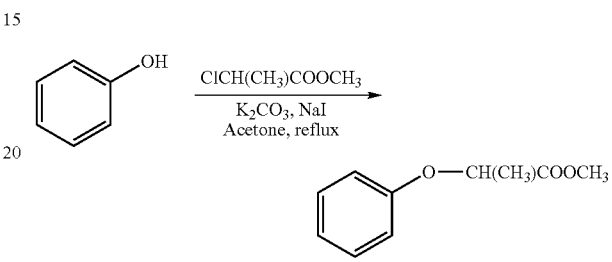

ε-Caprolactone is a cyclic monomer and is reactive, and the polymers derived are useful for tailoring specialty polyols and hydroxy-functional polymer resins with enhanced flexibility. The monomer polymerizes under mild conditions to give low viscosity products superior to conventional aliphatic polyesters. Copolymers of caprolactone with glycolide and lactide exhibit unique physical and biological properties as well as different hydrolysis profiles based on the composition of the monomers. The process of attaching an open chain ε-caprolactone moiety to the phenolic amino acid is defined as caprolation and will be referred to as such in describing this invention:

p-Dioxanone (1,4-dioxan-2-one) is a cyclic monomer and polymers are made via ring opening polymerization. Polyesters derived from this monomer are used in making absorbable surgical devices with longer absorption profile (slower hydrolysis) compare to polyglycolic acid. The absorbable surgical devices made from 1,4-dioxan-2-one are proved to be biologically safe, and biocompatible. The process of attaching an open chain p-dioxanone moiety (dioxanone) to the phenolic amino acid is defined as dioxonation and will be referred to as such in describing this invention:

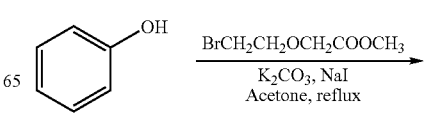

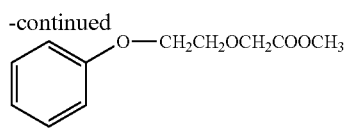

The functionalized amino acids of the present invention can be prepared according to any recognized method, including the Williamson ether synthesis.

Williamson Synthesis

Preparation of Ethers is an Important Reaction for which a Wide Variety of procedures have been developed during the last 100 years. The most commonly used method for the preparation of symmetrical and unsymmetrical ethers is the Williamson synthesis, involving a halide and an alkoxide. It is possible to mix the halide and alcohol with solid KOH and DMSO. The reaction involves an SN2 reaction in which an alkoxide ion replaces a halogen, sulfonyl, or a sulfate group. Usually, alkyl halides are used. The alkoxide can be prepared by the reaction of the corresponding alcohol with an active metal such as metallic sodium or a metal hydride like NaH acting upon the alcohol. The resulting alkoxide salt is then reacted with the alkyl halide (sulfonate or sulfate) to produce the ether in an SN2 reaction.

Recently several new procedures for Williamson synthesis have developed in which the phase transfer catalysis (PTC) appear to very convenient and the reactions can be run under mild conditions with high yields. Most recently, it was reported that ethers could be prepared directly from alcohol and alkyl halides under microwave irradiation in the presence of a quaternary ammonium salt.

For the synthesis of aromatic ethers, the phenolic compound was reacted with one member of the group Na metal, NaH, and potassium carbonate to form a phenoxide and then reacted with an alkyl halide to form an aromatic ether as shown below:

The first step of the Williamson ether synthesis is the reaction of sodium hydride with a phenolic compound. Phenols are more acidic than alkanols because of resonance stabilization of the conjugated anion.

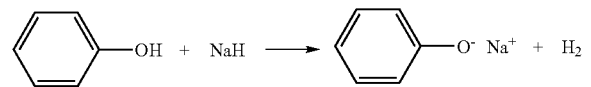

The resulting phenoxide ion is a powerful nucleophile, and reacts well with alkyl halide to form an ether.

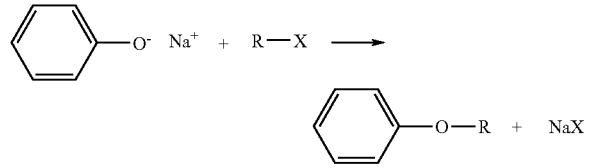

The alkyl halide should be primary so that the backside attack is not sterically hindered. When it is not primary, elimination usually results.

The general procedure for functionalizing phenolic compounds: to a mixture of phenolic compound, anhydrous potassium carbonate, sodium iodide, and disodium phosphate in anhydrous acetone, while refluxing, the alkyl halide is added and refluxed for a period of from a few hours to several days until the reaction is essentially complete. Then the acetone is distilled off, water is added, and crude product is filtered and recrystallized from a solvent or mixture of solvents. Some times the products are purified by column chromatography. Solvent systems, reaction conditions, and purification methods are modified based on the phenol compound.

The process of preparing a phenolic ester with glycolic acid is shown below:

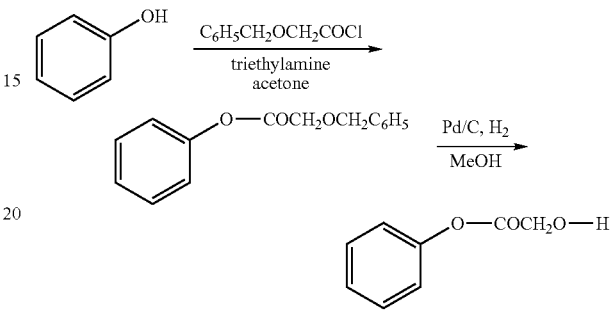

Benzyloxy acetyl chloride ($C_6H_5CH_2OCH_2COCl$) can be prepared as described in the following reaction scheme:

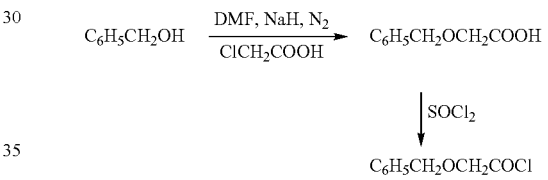

Using a similar method, $C_6H_5CH_2OCH(CH_3)COCl$, $C_6H_5CH_2O(CH_2)_5COCl$, and $C_6H_5CH_2OCH_2CH_2OCH_2COCl$ were synthesized for preparation of phenolic esters of amino acids.

Lactic acid can function as both an acid and an alcohol. This dual functionality leads to a variety of chemical reactions and valuable physical properties. The process of preparing a phenolic ester with lactic acid is shown below:

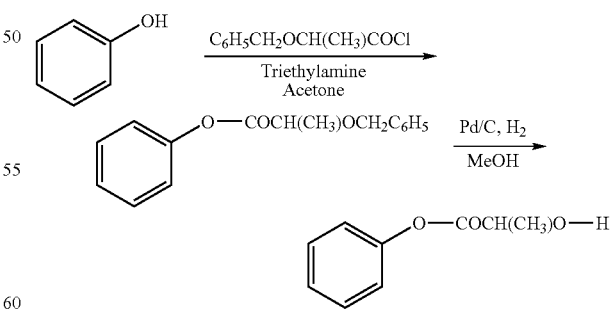

ϵ-Caprolactone, can function as both an acid and an alcohol. This dual functionality leads to a variety of chemical reactions and valuable physical properties. The process of preparing a phenolic ester with ϵ-caprolactone is shown below:

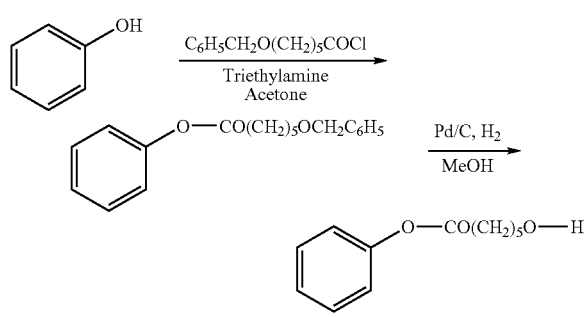

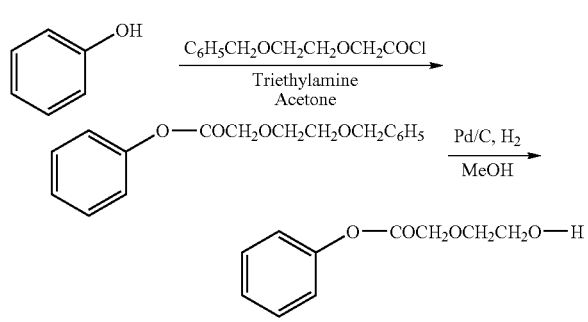

p-Dioxanone can function as both an acid and an alcohol. This dual functionality leads to a variety of chemical reactions and valuable physical properties. The process of preparing a phenolic ester with p-dioxanone is shown below:

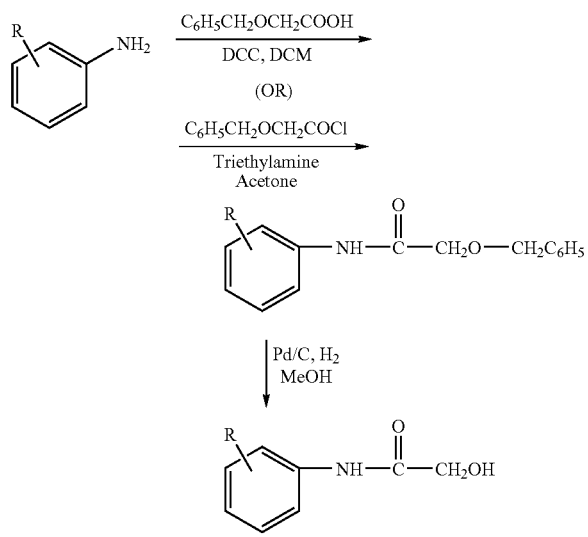

Synthesis of Phenolic amides:

Benzyloxyamides are prepared by reacting benzyloxy acetic acid with an amine using dicyclohexylcarbodiimide (DCC) as coupling agent, in dichloromethane (DCM) as a solvent. The amine is dissolved in DCM and benzyloxyacetic acid is added. While maintaining below room temperature, DCC solution in DCM is added dropwise. The reaction generally proceeds cleanly for the formation of an amide. The urea formed is not soluble in DCM, and the urea can be filtered off to get the amide. In a second method the amines are reacted with the acid chloride directly using a base, such as $K_2CO_3$, $NaHCO_3$ or triethyl amine to neutralize the HCl that is formed during the reaction. Acetone is a good solvent for this reaction. Both methods are suitable for preparing benzyloxyamides.

Synthesis of Phenolic esters:

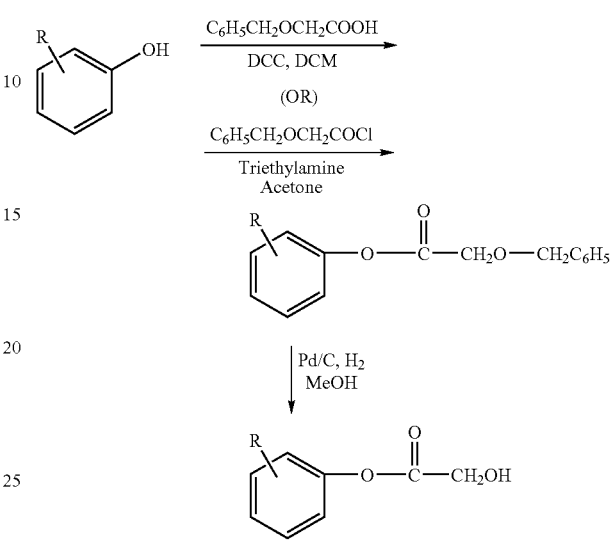

Conditions similar to those listed above can be used for preparing benzyloxyesters.

Debenzylation

Debenzylations were done using 50% wet Pd/C (5%) with hydrogen pressure up to 4 kg. MeOH or DMF can be as solvents. Dry Pd/C (5%) can be also used to avoid any moisture to avoid ester hydrolysis. DMF, MeOH, or Ethyl acetate can be used for this reaction.

Biodegradable Chewing Gums

After conventional chewing gum is chewed, the gum cud that remains that must be discarded. Unfortunately, conventional gum cuds can easily adhere to any dry surface, such as wood, concrete, paper and cloth. When gum cuds are improperly discarded, they can be difficult to remove from such surfaces, causing some environmental concerns. Recently, there has been a move to develop a chewing gum which is either ingestible or that creates a gum cud that is easily removable and degradable. Therefore, one of the objects of the present invention is to develop hydrolyzable and flexible elastomers that can be used in conventional and specialized biomedical chewing gum. Some of the compositions of the present invention can provide improved chewing gum and gum bases. The improved chewing gum and gum bases are biodegradable and do not cause environmental concerns if improperly discarded.

Bioactive Formulations

In other aspects of the present invention some functionalized phenolic amino acids of the present invention are further manufactured into formulations suitable for oral, rectal, parenteral (for example, subcutaneous, intramuscular, intradermal, or intravenous), transdermal, vitreal or topical administration. The most suitable route in any given case will depend on the nature and severity of the condition being treated and on the nature of the particular active compound that is being used. The formulations of a pharmaceutical composition are typically admixed with one or more pharmaceutically or veterinarially acceptable carriers and/or excipients as are well known in the art.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion.

Compositions of the present invention suitable for parenteral administration conveniently comprise sterile aqueous preparations of the active compounds, which preparations are preferably isotonic with the blood of the intended recipient.

Formulations suitable for rectal administration are preferably presented as unit dose suppositories.

Formulations suitable for ocular or vitreal administration may be presented as bioabsorbable coatings for implantable medical devices, injectables, liquids, gels or suspensions.

Formulations or compositions suitable for topical administration to the skin preferably take the form of an ointment, cream, lotion, paste, gel, spray, aerosol, or oil. Examples of carriers that conventionally used include Vaseline, lanoline, polyethylene glycols, alcohols, and combination of two or more thereof.

Formulations suitable for transdermal administration may be presented as discrete patches adapted to remain in intimate contact with the epidermis of the recipient for a prolonged period of time.

The active compounds may be provided in the form of foodstuffs or nutrition supplements, such as being added to, admixed into, coated, combined or otherwise added to a foodstuff. The term foodstuff is used in its widest possible sense and includes liquid formulations such as drinks including dairy products, biodegradable chewing gums, and other foods, such as health bars, desserts, etc. Food formulations containing compounds of the invention can be readily prepared according to standard practices.

Compounds of the formula used as medicaments or pharmaceuticals are typically administered in a manner and amount as is conventionally practiced. See, for example, Goodman and Gilman, *The Pharmaceutical Basis of Therapeutics*, current edition.

Compounds of the present invention have potent antioxidant activity and increased acidity of their phenolic component, as well as the improved biodegradation provided by the functionalization, and thus find wide application in pharmaceutical and veterinary uses, in cosmetics such as more effective skin creams to prevent skin ageing, in sun screens, in foods, health drinks, nutritional supplements, shampoos, and the like.

Examples of preparing the functionalized amino acids of the present invention are provided for some embodiments of the current invention. It can be extended to many other species. This selection is not meant to limit the scope of the invention in any way. Other variations in the procedure may be readily apparent to those skilled in the art.

Example-1

2-Amino-3-(4-hydroxy-phenyl)-propionic acid methyl ester

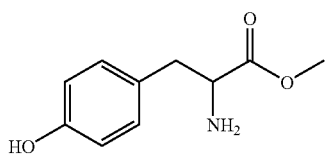

To a mixture of L-Tyrosine (50 grams, 275.95 mmol) in methanol (875 mL) at 0° C. was bubbled anhydrous hydrochloric acid for 5 hours, later stirred at room temperature for 17 hours. Methanol was distilled under vacuum below 40° C., ice cold water (100 mL) was added and the pH adjusted to 8 with aqueous ammonia. The crude 1 was filtered, dried and recrystallised from Ethylacetate to get pure 1 (40 grams, 74.3%) as cream color shining powder.

The melting point was measured for all the products by using Polmon (MP 96) melting point apparatus, and the melting point was found to be 134.5-135.5° C. (lit 135-139° C.). For all the products, NMR was run using Varian 200 MHz and tetramethylsilane as an internal standard.

Example-2

2-Acetylamino-3-(4-hydroxy-phenyl)-propionic acid methyl ester

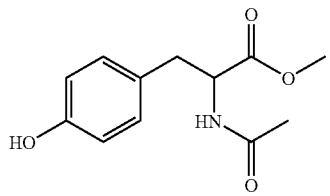

To a solution of 2-Amino-3-(4-hydroxy-phenyl)-propionic acid methyl ester 1 (10 grams, 51.28 mmol) in chloroform (60 mL) and 10% sodium carbonate solution (88 mL) at 0° C. was added acetyl chloride (4.01 grams, 51.08 mmol) drop wise and stirred at 40° C. for 10 hours. The crude 2 was filtered, dried and recrystallised from Ethylacetate to get pure 2 (6 grams, 49.4%) as white shining powder. M.p: 134-135.5 (lit 134-135.5° C.). $^1$H NMR (DMSO-$d_6$) δ 1.94 (s, 3H, COCH$_3$), 2.92 (q, 2H, CH$_2$), 3.70 (s, 3H, Ester), 4.61 (q, 1H, CH), 6.70 (d, 2H, Ar), 6.92 (d, 2H, Ar), 7.46 (d, 1H, NH), 8.86 (s, 1H, OH).

Example-3

2-Acetylamino-3-(4-methoxycarbonylmethoxy-phenyl)-propionic acid methyl ester

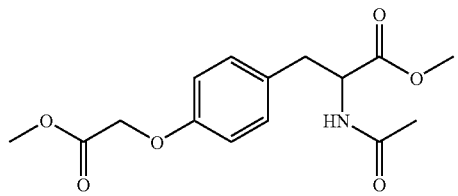

To a mixture of 2-Acetylamino-3-(4-hydroxy-phenyl)-propionic acid methyl ester 2 (15 grams, 63.29 mmol), potassium carbonate (35 grams, 253.25 mmol), sodium iodide (6 grams, 40 mmol), Disodium phosphate (9 grams, 63.75 mmol) in acetone (150 mL) was added methyl chloro acetate (10.4 grams, 95.83 mmol) and refluxed for 7 hours. Acetone was distilled and water (100 mL) was added. Crude 3 was filtered, dried and recrystallised from a mixture of chloroform:Hexane (1:6) to get pure 3 (13 grams, 66.5%) as a white powder. M.p: 113-115° C. $^1$H NMR (CDCl$_3$) δ 2.00 (s, 3H, COCH$_3$), 3.72 (s, 3H, Ester), 3.82 (s, 3H, Ester), 4.61 (s, 2H, CH$_2$), 4.84 (q, 1H, CH), 5.98 (d, 1H, NH), 6.82 (d, 2H, Ar), 7.02 (d, 2H, Ar).

Example-4

2-Acetylamino-3-(4-hydroxy-phenyl)-propionic acid

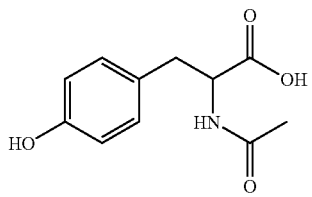

To a solution of 2-Acetylamino-3-(4-hydroxy-phenyl)-propionic acid methyl ester 2 (5 grams, 21.07 mmol) in Tetrahydrofuran (25 mL) was added 10% lithium hydroxide solution (10 mL) and heated at 60° C. for 1 hour. The reaction mass was cooled to room temperature and the pH adjusted to 4 with dilute hydrochloric acid, the organic phase separated and distilled to get crude amide 4, which was taken to next stage without purification.

Example-5

2-Acetylamino-3-(4-hydroxy-phenyl)-propionic acid methoxycarbonylmethyl ester

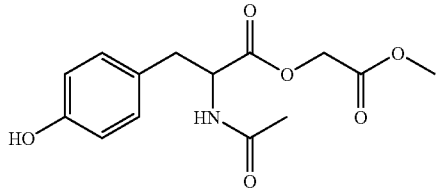

To a mixture of crude 2-Acetylamino-3-(4-hydroxy-phenyl)-propionic acid, Triethyl amine 4 (24 grams 23.71 mmol) in acetone (200 mL) was added methyl chloro acetate (2.35 grams, 21.65 mmol) and heated to reflux for 48 hours. The solids were filtered off, acetone distilled and water (10 mL) was added. Crude 5 extracted into chloroform, washed with 5% sodium bicarbonate (2×5 mL), water (2×5 mL), dried over sodium sulphate, distilled and purified by column chromatography on silica gel using chloroform:Ethylacetate (9:1) as eluant to get white powder, and the structure was confirmed by NMR. $^1$H NMR (CDCl$_3$) δ 1.98 (s, 3H, COCH$_3$), 3.04 & 3.20 (2dd, 2H, CH$_2$), 3.80 (s, 3H, Ester), 4.68 (q, 2H, CH$_2$), 4.98 (q, 1H, CH), 6.06 (d, 1H, NH), 6.34 (s, 1H, OH), 6.75 (d, 2H, Ar), 7.06 (d, 2H, Ar).

Example-6

2-Acetylamino-3-(4-methoxycarbonylmethoxy-phenyl)-propionic acid methoxycarbonyl methyl ester

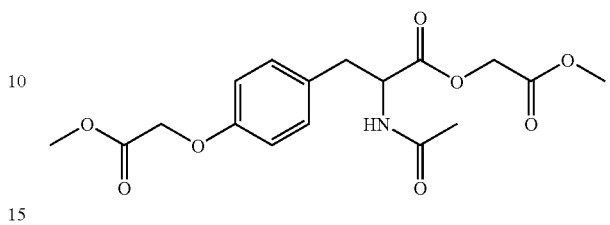

To mixture of 2-Acetylamino-3-(4-hydroxy-phenyl)-propionic acid methoxycarbonylmethyl ester 5 (5 grams, 16.95 mmol) Potassium carbonate (9.4 grams, 68 mmol) sodium iodide (1 gram, 6.67 mmol) Disodium Phosphate (1 gram, 70.84 mmol) in acetone (50 mL) is added Methyl chloroacetate (2.2 grams, 20.27 mmol) and is refluxed till the reaction complies by TLC. Acetone is distilled, water is added and the crude 6 can be extracted into chloroform, dried over sodium sulphate and distilled.

Example-7

2-Acetylamino-3-(4-carboxymethoxy-phenyl)-propionic acid

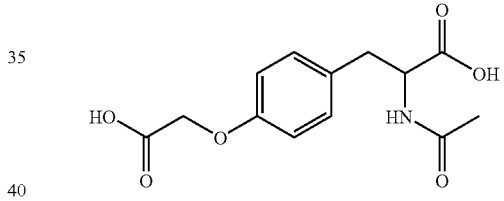

2-Acetylamino-3-(4-methoxycarbonylmethoxy-phenyl)-propionic acid methyl ester 3 (5 grams, 16.18 mmol) was added to a solution of sodium hydroxide (1.5 grams, 37.5 mmol) in water (50 mL) and heated to 60° C. for 5 hours. The reaction mass was cooled to room temperature, and the pH made acidic with acetic acid. Crude 7 was extracted into Ethylacetate, dried over sodium sulphate, distilled to get crude 7 (4 grams, 87.3%), which was carried over to next reaction.

Example-8

2-Acetylamino-3-(4-methoxycarbonylmethoxycarbonylmethoxy-phenyl)-propionic acid methoxycarbonylmethyl ester

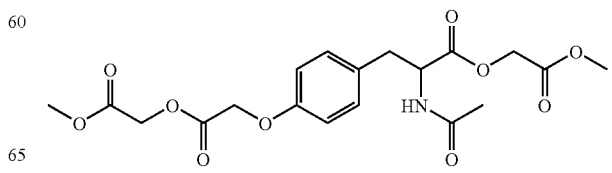

To a mixture of 2-Acetylamino-3-(4-carboxymethoxy-phenyl)-propionic acid 7 (4 grams, 14.23 mmol), Triethylamine (5.8 grams, 57.31 mmol) in acetone (25 mL) was added methyl chloro acetate (6.2 grams, 57.13 mmol) and refluxed for 5 hours. The solids were filtered off, acetone distilled and water (20 mL) added. Crude 8 was extracted into chloroform, washed with 5% sodium bicarbonate (2×10 mL), water (2×10 mL), dried over sodium sulphate, distilled. Crude 8 was recrystallised from a mixture of chloroform: Hexane (1:6) get pure 8 (3 grams, 49.66%) as white powder. M.p: 93-96° C. $^1$H NMR (CDCl$_3$) δ 1.96 (s, 3H, COCH$_3$), 3.12 (m, 2H, CH$_2$), 3.80 (s, 6H, 2×Ester), 4.56 (d, 2H, CH$_2$), 4.70 (s, 4H, 2×CH$_2$), 4.90 (q, 1H, CH), 5.86 (d, 1H, NH), 6.85 (d, 2H, Ar), 7.12 (d, 2H, Ar).

Example-9

2-Acetylamino-3-[4-(2-benzyloxy-acetoxy)-phenyl]-propionic acid methyl ester

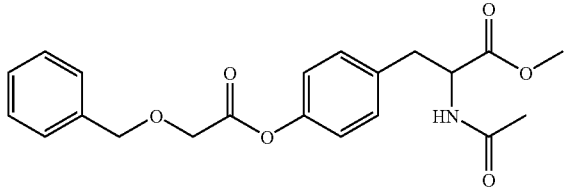

To a mixture of 2-Acetylamino-3-(4-methoxycarbonyl-methoxy-phenyl)-propionic acid methyl ester 2 (9 grams, 37.97 mmol), Triethylamine (9.8 grams, 96.84 mmol) in dichloromethane (90 mL) at 0° C. was added benzyloxy acetyl chloride (10.5 grams, 56.91 mmol) drop wise, later stirred at room temperature for 24 hours. The solids were filtered off, the dichloromethane layer was washed with 5% sodium bicarbonate (2×20 mL), water (2×20 mL), dried over sodium sulphate, distilled and purified by recrystallisation in a mixture of chloroform:hexane (1:6) to get pure 9 (10 grams, 68.4%) as a white powder. M.p: 90.8-92.2° C. $^1$H NMR (CDCl$_3$) δ 2.00 (s, 3H, COCH$_3$), 3.10 (d, 2H, CH$_2$), 3.74 (s, 3H, Ester), 4.34 (s, 2H, CH$_2$), 4.72 (s, 2H, CH$_2$), 4.85 (q, 1H, CH), 6.15 (d, 1H, NH), 7.08 (m, 5H, Ar), 7.38 (m, 4H, Ar).

Example-10

2-Acetylamino-3-[4-(2-hydroxy-acetoxy)-phenyl]-propionic acid methyl ester

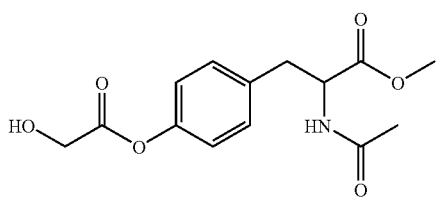

2-Acetylamino-3-[4-(2-benzyloxy-acetoxy)-phenyl]-propionic acid methyl ester 9 (5 grams, 12.98 mmol) is dissolved in Ethyl acetate (100 mL) in pressure vessel, palladium on carbon (5%, 2 grams) was added and the mixture stirred under an atmosphere of hydrogen (3.5 Kg) for 6 hours. The catalyst was removed by filtration and distilled off ethyl acetate. The crude 10 was purified by recrystallisation in a mixture of chloroform:hexane (1:6) to get pure 10 (2.5 grams, 65.2%) as a white powder. M.p: 132-134° C. $^1$H NMR (CDCl$_3$) δ 2.00 (s, 3H, COCH$_3$), 2.68 (t, 1H, OH), 3.12 (m, 2H, CH$_2$), 3.74 (s, 3H, Ester), 4.40 (d, 2H, CH$_2$), 4.85 (q, 1H, CH), 6.04 (d, 1H, NH), 7.04 (d, 2H, Ar), 7.12 (d, 2H, Ar).

Example-11

3-(4-Hydroxy-phenyl)-2-phenethyloxycarbonylamino-propionic acid methyl ester

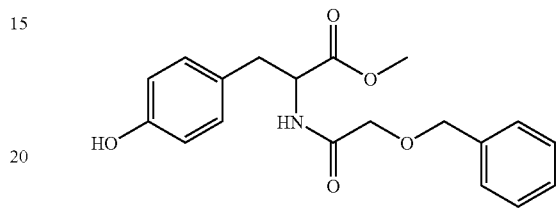

To a mixture of 2-Amino-3-(4-hydroxy-phenyl)-propionic acid methyl ester 1 (5 grams, 25.61 mmol), sodium bicarbonate (2.3 grams, 27.37 mmol) in Ethylacetate (100 mL) at 0° C. was added benzyloxy acetyl chloride (5.2 grams, 28.18 mmol) drop wise, later stirred at room temperature for 5 hours. The solids were filtered off, Ethylacetate layer washed with 5% sodium bicarbonate (2×10 mL), water (2×10 mL), dried over sodium sulphate, distilled and purified by column chromatography on silica gel using benzene as eluant to get pure 11 (5 grams, 62.8%) as a white powder. M.p: 68-70° C. $^1$H NMR (CDCl$_3$) δ 3.14 (m, 2H, CH$_2$), 3.74 (s, 3H, Ester), 3.94 (s, 2H, CH$_2$), 4.48 (d, 2H, CH$_2$), 4.90 (q, 1H, CH), 6.64 (d, 2H, Ar), 6.92 (d, 2H, Ar), 7.08 (d, 1H, NH), 7.30 (m, 5H, Ar).

Example-12

2-(2-Hydroxy-acetylamino)-3-(4-hydroxy-phenyl)-propionic acid methyl ester

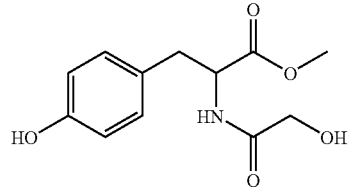

3-(4-Hydroxy-phenyl)-2-phenethyloxycarbonylamino-propionic acid methyl ester 11 (5 grams, 14.57 mmol) was dissolved in methanol (25 mL) in a pressure vessel, palladium on carbon (5%, 3 grams) added and the mixture stirred under an atmosphere of hydrogen (3 Kg) for 24 hours. The catalyst was removed by filtration, and distilled off the methanol. The crude 12 was purified by column chromatography on silica gel using chloroform as eluant to get pure 12 (2.5 grams, 67.9%) as a light yellow syrup and which crystallized very slowly to a white powder and further recrystallised in a mixture of Ethyl acetate:Hexane (1:6) to give pure 12 (2 grams) as a white powder. M.p: 57-58° C. $^1$H NMR (CDCl$_3$+DMSO-d$_6$) δ 3.00 (d, 2H, CH$_2$), 3.70 (s, 3H, Ester), 3.90 (d, 2H, CH$_2$), 4.68 (q, 1H, CH), 5.38 (t, 1H, OH), 6.68 (d, 2H, Ar), 6.92 (d, 2H, Ar), 7.40 (d, 1H, NH), 8.84 (s, 1H, OH).

Example-13

3-(4-Hydroxy-benzyl)-morpholine-2,5-dione

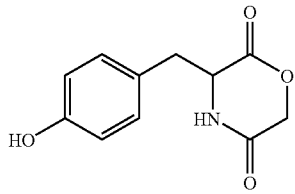

To mixture of 2-(2-Hydroxy-acetylamino)-3-(4-hydroxy-phenyl)-propionic acid methyl ester 12 (5 grams, 19.76 mmol) in Toluene (100 mL) is added Para toluene sulfuric acid (100 mg) and refluxed for long hours till the disappearance of starting material on TLC. The toluene layer is washed with 5% sodium bicarbonate solution, water, dried over sodium sulphate and can be distilled to get 13.

Example-14

2-(2-Benzyloxy-acetylamino)-3-(4-methoxycarbonylmethoxy-phenyl)-propionic acid methyl ester

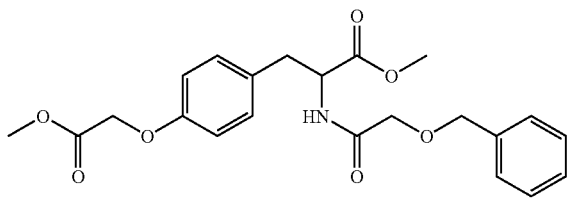

To a mixture of 3-(4-Hydroxy-phenyl)-2-phenethyloxycarbonylamino-propionic acid methyl ester 11 (5 grams, 14.57 mmol), potassium carbonate (6 grams, 43.4 mmol), sodium iodide (0.5 grams, 3.33 mmol), Disodium phosphate (0.5 grams, 3.54 mmol) in acetone (30 mL) was added methyl chloro acetate (2.5 grams, 23 mmol) and heated to reflux for 10 hours. Acetone was distilled and water (30 mL) we added and extracted with chloroform, dried over sodium sulphate and distilled to give crude 14, which was purified by column chromatography on silica gel using chloroform as eluant to get pure 14 (4 grams, 66.6%) as a syrup. $^1$H NMR (CDCl$_3$) δ 3.18 (d, 2H, CH$_2$), 3.72 (s, 3H, Ester), 3.78 (s, 3H, Ester), 3.94 (s, 2H, CH$_2$), 4.50 (d, 2H, CH$_2$), 4.58 (s, 2H, CH$_2$), 4.88 (q, 1H, CH), 6.78 (d, 2H, Ar), 7.00 (d, 3H, Ar & NH), 7.28 (m, 5H, Ar).

Example-15

2-(2-Hydroxy-acetylamino)-3-(4-methoxycarbonylmethoxy-phenyl)-propionic acid methyl ester

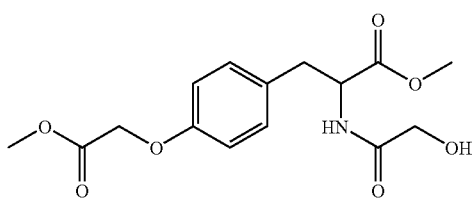

2-(2-Benzyloxy-acetylamino)-3-(4-methoxycarbonylmethoxy-phenyl)-propionic acid methyl ester 14 (3.5 grams, 8.43 mmol) was dissolved in methanol (100 mL) in a pressure vessel, palladium on carbon (5%, 3 grams, 50% wet) added and the mixture stirred under an atmosphere of hydrogen (3.5 Kg) for 3.5 hrs. The catalyst is removed by filtration and distilled off methanol. The crude 15 was purified by column chromatography on silica gel using chloroform as eluant to get pure 15 (1.8 grams, 65.6%) as a light yellow Syrup. $^1$H NMR (CDCl$_3$) δ 3.18 (m, 2H, CH$_2$), 3.44 (s, 1H, OH), 3.72 (s, 3H, Ester), 3.82 (s, 3H, Ester), 4.02 (s, 2H, CH$_2$), 4.60 (s, 2H, CH$_2$), 4.84 (q, 1H, CH), 6.82 (d, 2H, Ar), 7.05 (d, 2H, Ar), 7.12 (d, 1H, NH).

Example-16

2-(2-Benzyloxy-acetylamino)-3-(4-hydroxy-phenyl)-propionic acid

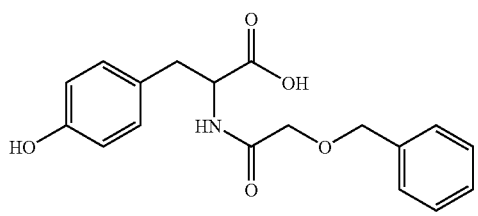

To a solution of 3-(4-Hydroxy-phenyl)-2-phenethyloxycarbonylamino-propionic acid methyl ester 11 (10 grams, 29.15 mmol) in Tetrahydrofuran (50 mL) was added, a solution of lithium hydroxide (1.75 grams) in water (5 mL) and stirred at 40° C. for 4 hrs. The reaction mixture pH was made acidic with acetic acid, separated the Organic layer and distilled to get crude 16 which was carried over to further reactions without characterization.

Example-17

2-(2-Benzyloxy-acetylamino)-3-(4-hydroxy-phenyl)-propionic acid methoxy carbonyl methyl ester

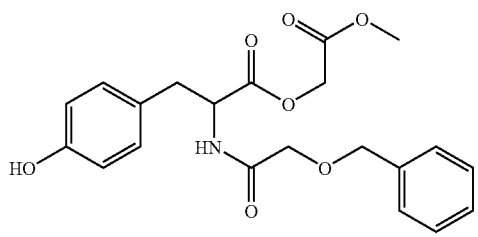

To a mixture of Crude 2-(2-Benzyloxy-acetylamino)-3-(4-hydroxy-phenyl)-propionic acid 16 (9.5 grams, 28.87 mmol) Triethylamine (6.96 grams, 68.78 mmol) in acetone (100 mL) was added Methyl chloroacetate (5.3 grams, 48.8 mmol) and heated to reflux for 16 hrs. The solids were filtered off, acetone distilled and water (25 mL) was added. Crude 17 extracted into chloroform, washed with 5% Sodium bicarbonate (2×25 mL), water (2×25 mL), dried over sodium sulphate, distilled and purified by column chromatography on silica gel using chloroform as eluant to get pure 17 (3.9 grams, 33.3%) as a White Powder. M.p: 93.5-96.2° C. $^1$H NMR (CDCl$_3$) δ 3.00 & 3.20 (2dd, 2H, CH$_2$), 3.78 (s, 3H, Ester), 3.92 (d, 2H, CH$_2$), 4.45 (d, 2H, CH$_2$), 4.60 & 4.76 (2d, 2H, CH$_2$), 4.98 (m, 1H, CH), 6.64 (d, 2H, Ar), 6.82 (s, 1H, OH), 7.00 (d, 2H, Ar), 7.30 (m, 6H, Ar & NH).

Example-18

2-(2-Hydroxy-acetylamino)-3-(4-hydroxy-phenyl)-propionic acid methoxy carbonyl methyl ester

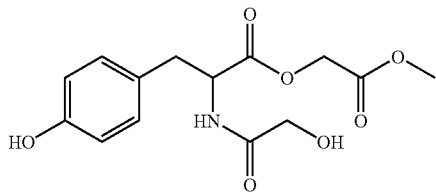

2-(2-Benzyloxy-acetylamino)-3-(4-hydroxy-phenyl)-propionic acid methoxy carbonyl methyl ester 17 (2.5 grams) was dissolved in ethyl acetate (50 mL) in a pressure vessel, palladium on carbon (5%, 2 grams) added and the mixture stirred under an atmosphere of hydrogen (3 Kg) for 16 hrs. The catalyst is removed by filtration and ethyl acetate can be distilled off to get 18.

Example-19

2-(2-Benzyloxy-acetylamino)-3-(4-methoxycarbonylmethoxy-phenyl)-propionic acid 2-methoxycarbonyl-ethyl ester

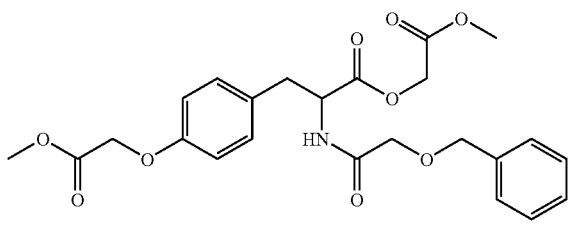

To a mixture of 2-(2-Benzyloxy-acetylamino)-3-(4-hydroxy-phenyl)-propionic acid methoxy carbonyl methyl ester 17 (5 grams, 12.46 mmol) Potassium carbonate (9 grams, 65.12 mmol) sodium iodide (3 grams, 20 mmol) in acetone (50 mL) was added Methyl chloroacetate (2.7 grams, 24.88 mmol) and heated to reflux for 16 hrs. Acetone distilled and water (50 mL) was added, extracted into chloroform, dried over sodium sulphate and distilled to get Crude 19, which was purified by recrystallisation in a mixture of chloroform:Hexane (1:6) to get pure 19 (3.8 grams, 64.5%) as a White Powder. M.p: 42-44° C. $^1$H NMR (CDCl$_3$) δ 3.18 (m, 2H, CH$_2$), 3.78 (s, 3H, Ester), 3.94 (s, 2H, CH$_2$), 4.40 (d, 2H, CH$_2$), 4.55 (s, 4H, 2×CH$_2$), 4.92 (q, 1H, CH), 6.75 (d, 2H, Ar), 6.95 (d, 1H, NH), 7.00 (d, 2H, Ar), 7.28 (m, 5H, Ar).

Example-20

2-(2-Hydroxy-acetylamino)-3-(4-methoxycarbonyl-methoxy-phenyl)-propionic acid methoxycarbonylmethyl ester

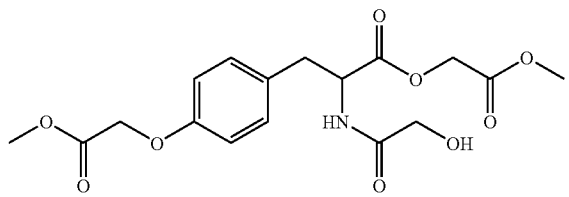

2-(2-Benzyloxy-acetylamino)-3-(4-methoxycarbonylmethoxy-phenyl)-propionic Acid 2-methoxy carbonyl-ethyl ester 19 (3.5 grams, 7.39 mmol) was dissolved in Methanol (100 mL) in a pressure vessel, palladium on carbon (5%, 3 grams) added and the mixture stirred under an atmosphere of hydrogen (3.5 Kg) for 6 hrs. The catalyst is removed by filtration, and distilled off methanol under vacuum to get crude 20 (1 grams) as light yellow syrup. $^1$H NMR (CDCl$_3$) δ 3.14 (m, 2H, CH$_2$), 3.74 (s, 3H, Ester), 3.76 (s, 3H, Ester), 3.90 (s, 2H, CH$_2$), 4.60 (s, 2H, CH$_2$), 4.62 (s, 2H, CH$_2$), 4.72 (s, 2H, CH$_2$), 4.90 (q, 1H, CH), 6.80 (d, 2H, Ar), 7.12 (d, 2H, Ar), 7.20 (d, 1H, NH).

Example-21

3-[4-(2-Benzyloxy-acetoxy)-phenyl]-2-(2-benzyloxy-acetylamino)-propionic acid methyl ester

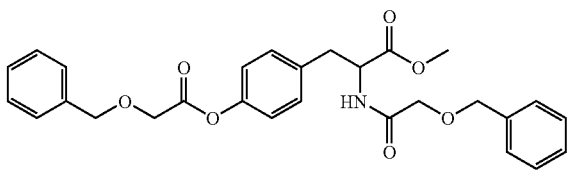

To mixture of Tyrosine methyl ester 1 (20 grams, 102.56 mmol) Triethylamine (33.4 grams, 330 mmol) in acetone (400 mL) was added Benzyloxy acetyl chloride (60 grams, 325.2 mmol) drop wise and further stirred for 48 hrs. The solids were filtered off, acetone distilled to get crude 21, which was purified column chromatography on silica gel using Benzene as eluant to get pure 21 (14 grams, 27.8%) as a light yellow Syrup. $^1$H NMR (CDCl$_3$) δ 3.12 (d, 2H, CH$_2$), 3.72 (s, 3H, Ester), 3.94 (s, 2H, CH$_2$), 4.28 (s, 2H, CH$_2$), 4.52 (d, 2H, CH$_2$), 4.70 (s, 2H, CH$_2$), 4.84 (q, 1H, CH), 7.00 (d, 2H, Ar), 7.10 (d, 2H, Ar), 7.32 (m, 6H, Ar+NH).

Example-22

3-[4-(2-Hydroxy-acetoxy)-phenyl]-2-(2-hydroxy-acetylamino)-propionic acid methyl ester

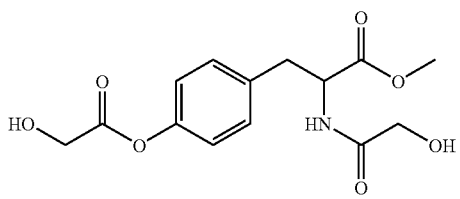

3-[4-(2-Benzyloxy-acetoxy)-phenyl]-2-(2-benzyloxy-acetylamino)-propionic acid methyl ester 21 (5 grams) is dissolved in Ethyl acetate (100 mL) in a pressure vessel, palladium on carbon (5%, 3 grams) added and the mixture stirred under an atmosphere of hydrogen (2 to 4 Kg) till the disappearance of starting material on TLC. The catalyst is removed by filtration and ethyl acetate distilled off to get 22

Example-23

3-[4-(2-Benzyloxy-acetoxy)-phenyl]-2-(2-benzyloxy-acetylamino)-propionic acid methoxycarbonyl-methyl ester

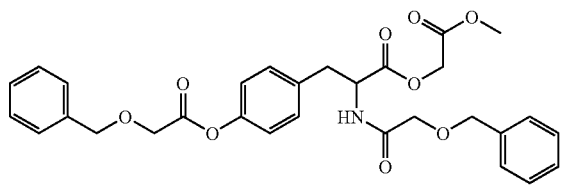

To mixture of 2-(2-Benzyloxy-acetylamino)-3-(4-hydroxy-phenyl)-propionic acid methoxy carbonyl methyl ester 17 (3 grams, 7.48 mmol), Triethyl amine (1.9 grams, 18.77 mmol) in acetone (50 mL) was added Benzyloxy acetyl chloride (2 grams, 10.8 mmol) drop wise and further stirred for 16 hrs. The solids were filtered off, Acetone distilled, extracted into chloroform washed with 5% sodium bicarbonate (2×10 mL), water (2×10 mL), dried over sodium sulphate and distilled to get crude 23, which was purified by column chromatography on silica gel using chloroform as eluant to get pure 23 (2.1 grams, 52.5%) as light yellow Syrup. $^1$H NMR (CDCl$_3$) δ 3.18 (m, 2H, CH$_2$), 3.76 (s, 3H, Ester), 3.94 (s, 2H, CH$_2$), 4.30 (s, 2H, CH$_2$), 4.48 (s, 2H, CH$_2$), 4.60 (s, 2H, CH$_2$), 4.72 (s, 2H, CH$_2$), 4.84 (q, 1H, CH), 7.00 (d, 2H, Ar), 7.30 (m, 12H, Ar).

Example-24

2-(2-Benzyloxy-acetylamino)-3-[4-(2-hydroxy-acetoxy)-phenyl]-propionic acid methoxycarbonylmethyl ester

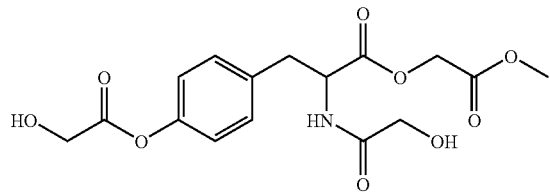

3-[4-(2-Benzyloxy-acetoxy)-phenyl]-2-(2-benzyloxy-acetylamino)-propionic acid methoxy carbonyl methyl ester 23 (2 grams, 3.73 mmol) was dissolved in Ethyl acetate (50 mL) in a pressure vessel, palladium on carbon (5%, 2 grams) added and the mixture stirred under an atmosphere of Hydrogen (3.5 Kg) for 6 hrs. The catalyst was removed by filtration, and distilled off Ethyl acetate to get crude 24, which was recrystallised in a mixture of chloroform:Hexane (1:6) to get pure 24 (0.7 grams, 51%) as white Powder. M.p: 116-118° C. $^1$H NMR (CDCl$_3$) δ 3.22 (m, 2H, CH$_2$), 3.78 (s, 3H, Ester), 3.98 (d, 2H, CH$_2$), 4.38 (d, 2H, CH$_2$), 4.75 (s, 2H, CH$_2$), 4.96 (q, 1H, CH), 5.16 (t, 2H, OH), 7.04 (d, 2H, Ar), 7.26 (d, 2H, Ar), 7.42 (d, 1H, NH).

In Vitro Hydrolysis of Functionalized Phenolics

A few selected compounds were examined for the rate of hydrolysis by conducting in vitro hydrolysis studies at reflux temperature (100° C.). For each experiment, 500 mg of a functionalized compound and 50 mL of pH 7.4 buffer solution (purchased from Aldrich chemical company) were charged into a 100 mL round bottom flask fitted with a condenser and the contents were refluxed. In vitro hydrolysis of the functionalized amino acid was monitored by thin layer chromatography (TLC) using corresponding starting material (original amino acid) as a control. In vitro hydrolysis was continued at reflux until the functionalized molecule hydrolyzed to the starting amino acid.

Example-25

2-Acetylamino-3-(4-hydroxy-phenyl)-propionic acid methoxycarbonylmethyl ester (example-5), was hydrolyzed under the above conditions in one hour as shown below:

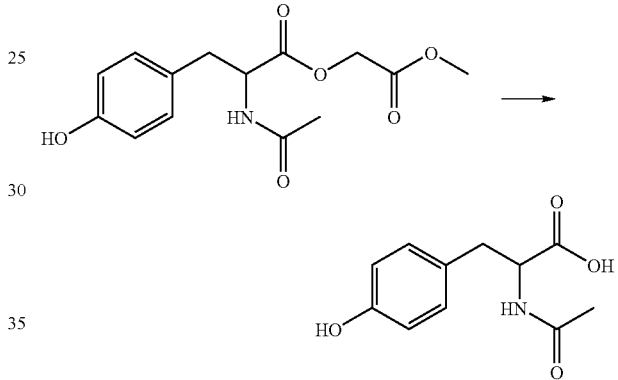

Example-26

2-Acetylamino-3-(4-methoxycarbonylmethoxycarbonylmethoxy-phenyl)-propionic acid methoxycarbonylmethyl ester (example-8) was hydrolyzed under the above conditions in one hour and thirty minutes as shown below:

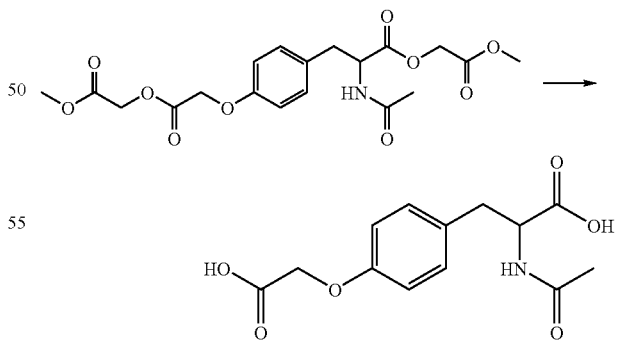

Example-27

Acetylamino-3-[4-(2-benzyloxy-acetoxy)-phenyl]-propionic acid methyl ester (example-9) was hydrolyzed under the above conditions in one hour and thirty minutes as shown below:

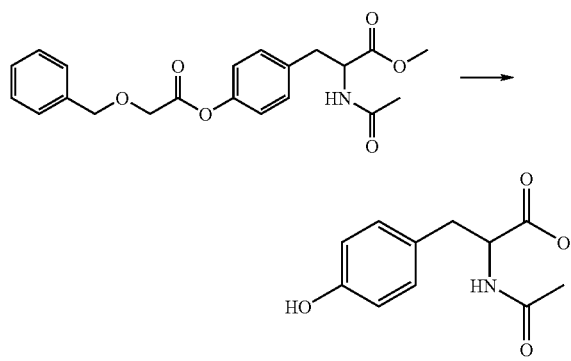

Example-28

2-(2-Benzyloxy-acetylamino)-3-(4-hydroxy-phenyl)-propionic acid methoxy carbonyl methyl ester (example-17) was hydrolyzed under the above conditions in one hour and thirty minutes as shown below:

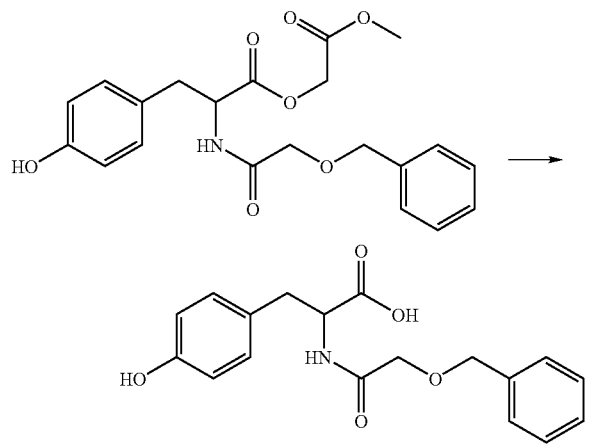

Example-29

2-(2-Benzyloxy-acetylamino)-3-(4-methoxycarbonyl-methoxy-phenyl)-propionic acid 2-methoxycarbonyl-ethyl ester (example-19) was hydrolyzed under the above conditions in one hour as shown below:

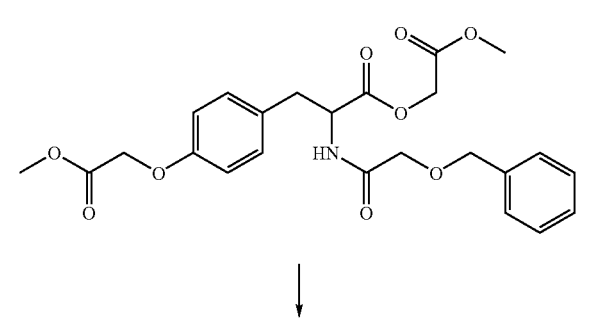

-continued

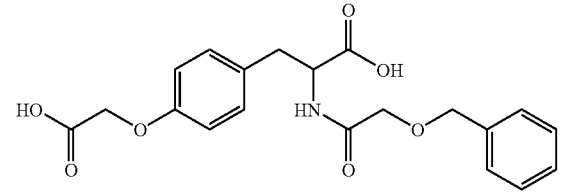

Example-30

2-(2-Benzyloxy-acetylamino)-3-[4-(2-hydroxy-acetoxy)-phenyl]-propionic acid methoxycarbonylmethyl ester (example-24) was hydrolyzed under the above conditions in one hour as shown below:

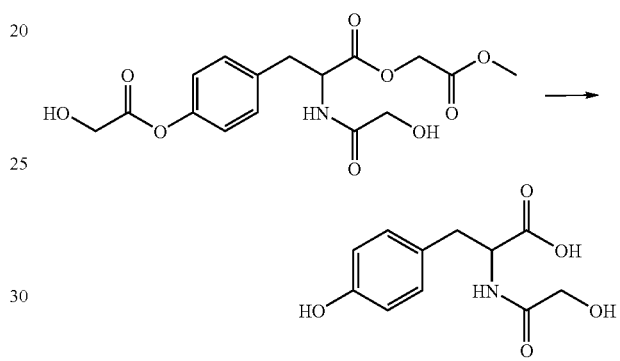

This indicates that the functionalized amino acids of the present invention hydrolyze and also that polymers derived from the functionalized amino acids should hydrolyze. Therefore, using the functionalized amino acids, one can develop polymers with controlled hydrolysis profiles.

What is claimed is:
1. A compound selected from:

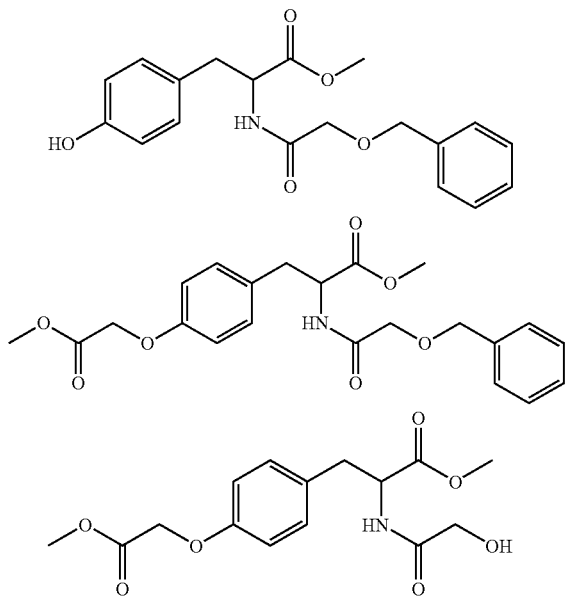

-continued

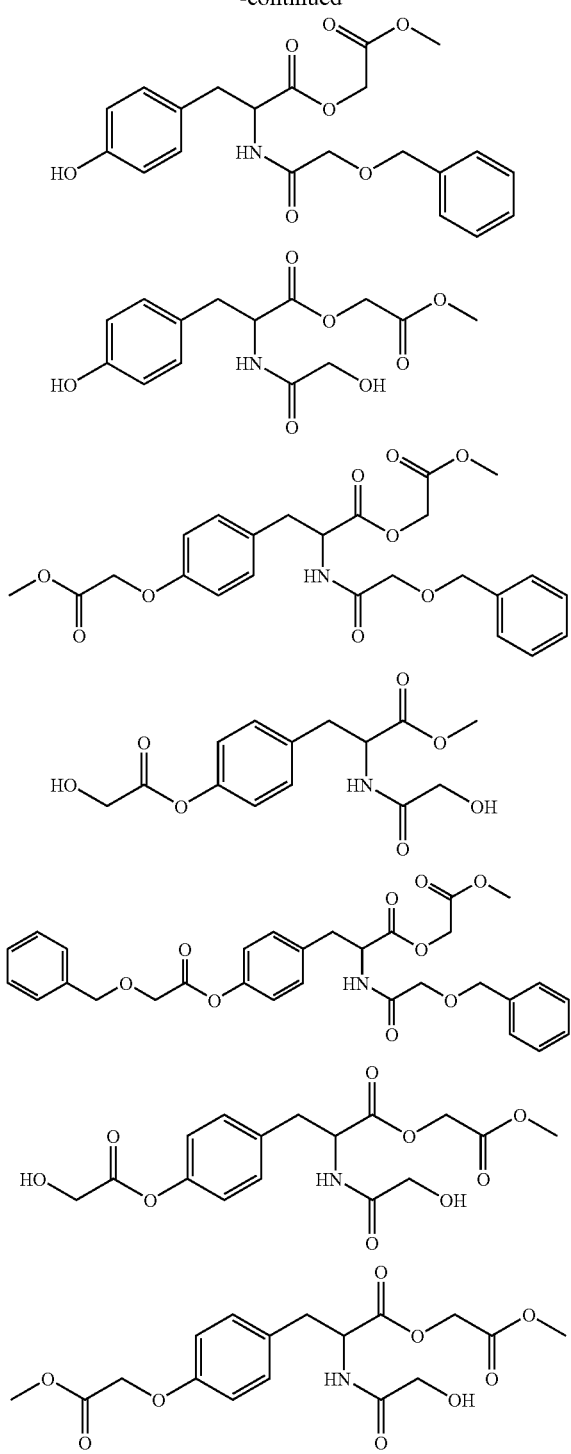

or a pharmaceutically acceptable salt or stereoisomer thereof.

2. A compound according to claim 1, wherein the compound is:

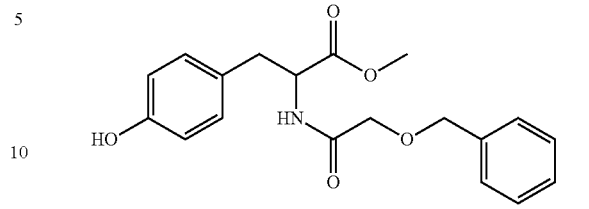

or a pharmaceutically acceptable salt or stereoisomer thereof.

3. A compound according to claim 1, wherein the compound is:

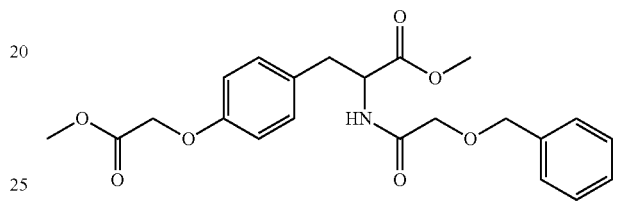

or a pharmaceutically acceptable salt or stereoisomer thereof.

4. A compound according to claim 1, wherein the compound is:

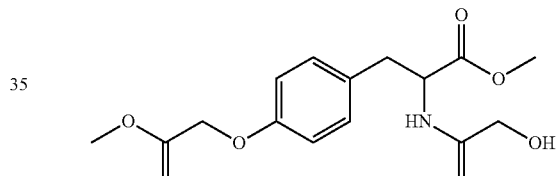

or a pharmaceutically acceptable salt or stereoisomer thereof.

5. A compound according to claim 1, wherein the compound is:

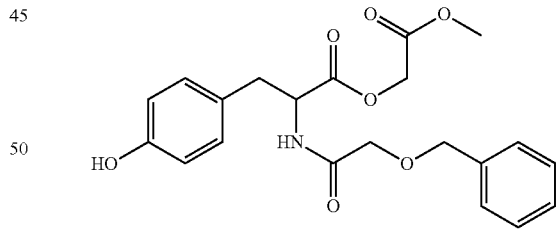

or a pharmaceutically acceptable salt or stereoisomer thereof.

6. A compound according to claim 1, wherein the compound is:

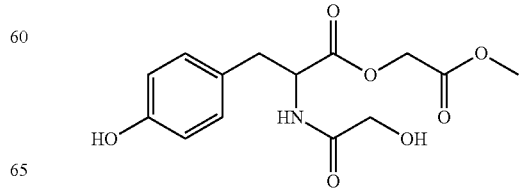

or a pharmaceutically acceptable salt or stereoisomer thereof.

7. A compound according to claim 1, wherein the compound is:

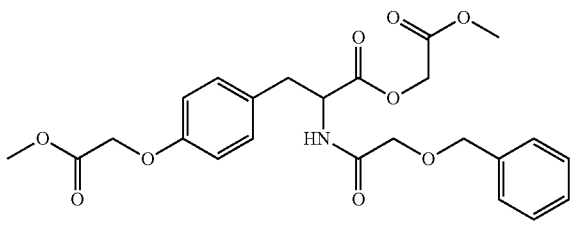

or a pharmaceutically acceptable salt or stereoisomer thereof.

8. A compound according to claim 1, wherein the compound is:

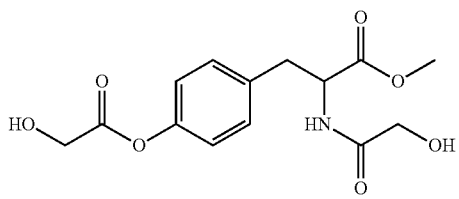

or a pharmaceutically acceptable salt or stereoisomer thereof.

9. A compound according to claim 1, wherein the compound is:

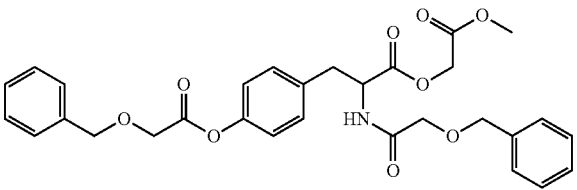

or a pharmaceutically acceptable salt or stereoisomer thereof.

10. A compound according to claim 1, wherein the compound is:

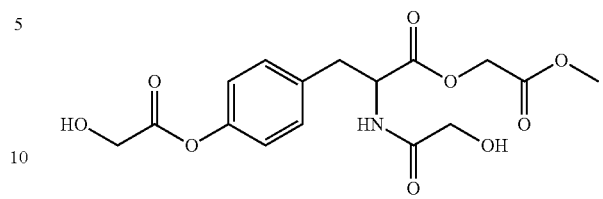

or a pharmaceutically acceptable salt or stereoisomer thereof.

11. A compound according to claim 1, wherein the compound is:

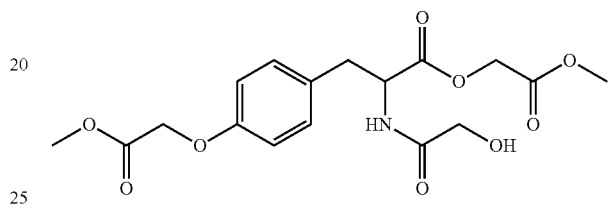

or a pharmaceutically acceptable salt or stereoisomer thereof.

12. A compound according to claim 1, wherein the compound is:

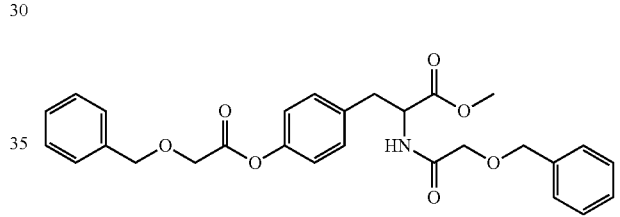

or a pharmaceutically acceptable salt or stereoisomer thereof.

* * * * *